US008142771B2

(12) United States Patent
Suo et al.

(10) Patent No.: US 8,142,771 B2
(45) Date of Patent: Mar. 27, 2012

(54) USE OF COCCIDIAN

(76) Inventors: Xun Suo, Beijing (CN); Xiaojia Wang, Beijing (CN); Xianyong Liu, Beijing (CN); Tuanyuan Shi, Beijing (CN); Lili Hao, Beijing (CN); Wenchao Yan, Beijing (CN); Hongyan Wang, Beijing (CN); Jianan Li, Beijing (CN)

( * ) Notice: Subject to any disclaimer, the term of this patent is extended or adjusted under 35 U.S.C. 154(b) by 108 days.

(21) Appl. No.: 12/593,851

(22) PCT Filed: Mar. 28, 2008

(86) PCT No.: PCT/CN2008/000621

§ 371 (c)(1),
(2), (4) Date: Sep. 29, 2009

(87) PCT Pub. No.: WO2008/119254

PCT Pub. Date: Oct. 9, 2008

(65) Prior Publication Data

US 2010/0183668 A1 Jul. 22, 2010

(30) Foreign Application Priority Data

Mar. 29, 2007 (CN) .......................... 2007 1 0064924

(51) Int. Cl.

| | |
|---|---|
| ***C12N 15/00*** | (2006.01) |
| ***A01N 63/00*** | (2006.01) |
| ***A01N 65/00*** | (2009.01) |
| ***A61K 48/00*** | (2006.01) |

(52) U.S. Cl. ................... 424/93.21; 424/93.1; 424/93.2; 435/320.1

(58) Field of Classification Search ........................ None
See application file for complete search history.

(56) References Cited

U.S. PATENT DOCUMENTS

| | | | | |
|---|---|---|---|---|
| 6,908,620 | B2 | 6/2005 | McDougald et al. | |
| 2003/0175287 | A1 * | 9/2003 | Medzhitov et al. | 424/185.1 |
| 2006/0121060 | A1 * | 6/2006 | Kappe et al. | 424/269.1 |

FOREIGN PATENT DOCUMENTS

CN 100998866 A 7/2007

OTHER PUBLICATIONS

Nishikawa et al. International Journal of Parasitology 33 (2003) 1525-1535.*

Meireles et al. (Brazilian Journal of Poultry Science Oct.-Dec. 2004, v.6, n.4 249-252).*

Luschow et al. Vaccine 19 (2001) 4249-4259.*

Geriletu et al., "Construction of two DNA vaccines chicken *E.tenella* and their expressions in chicken muscles", Journal of Northwest Sci-Tech University of Agri. and For. (Nat. Sci. Ed.), Dec. 2005, vol. 33, No. 112, p. 34-38, 42.

Hao, Lili et al., "A transgenic coccidian system for expressing and transporting viral protein of important poultry disease—a production system of high capacity live vector-based vaccine for inducing protective mucosal immunity and cellular immunity efficiently", Proceedings of Ninth Conference of Chinese Society of Veterinary Preliminary Parasitology, 2006, p. 52.

* cited by examiner

*Primary Examiner* — Oluwatosin Ogunbiyi

(74) *Attorney, Agent, or Firm* — Morriss O'Bryant Compagni

(57) ABSTRACT

The present invention provides a novel use of coccidian, specifically relates to the use of coccidian as a vaccine live vector. The present invention further provides a live vaccine with coccidian as a vector, which is transgenic coccidian capable of expressing exogenous protein or stably transfected coccidian that contain expression vector and can express exogenous coccidian. The present coccidian vector live vaccine can induce organisms to simultaneously generate protective humoral and cellular immune responses (including the mucosal immune response), as well as generate memory responses, which can be readily carried out and has stable effect and high biological safety without generating immune tolerance.

9 Claims, 3 Drawing Sheets

```
SEQUENCE LISTING

<160> NUMBER OF SEQ ID NOS: 14

<210> SEQ ID NO 1
<211> LENGTH: 14355
<212> TYPE: DNA
<213> ORGANISM: Artificial Sequence
<220> FEATURE:
<223> OTHER INFORMATION: Sequence of expression vector pHDEA-TFP

<400> SEQUENCE: 1

tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgaa    240

ccagcaaagg tagcaacagt agaggttagc aatgttacct ttgtcaccgt cagtgacagg    300

cacaagaacg aacttgttac actcgagata catagcttct gtaaaactga atcattcgcg    360

gtttctgttt gctctgctga catctattgg tccattgttg gagactctgt tgctttttct    420

gtttttttaaa ttcttataga acccgctatt gctgtcgtgg tgagccatcc gccgcgaaac    480

ggctgatgct cgactcattg tggctgcttt gcccattcgc tgcggttagt tgcagaaaaa    540

aacagcggca caaatagctg ctcccccagg tgataatatc tctacaacag cattctagga    600

tgtgcttgaa tgtcccgccc tcttcctttc caaatagttg ctcgcgcagt tgatgatatc    660

gtaacagcag cgttctagtg agtatttgaa tacccagccc tgttgttttc aaagccacgc    720

aacagcagca gttacagaag catataaagc ccatgcagct gatgctgctg cagctgaact    780

ctctactggg aaaagcatgc atcatgcaaa atgctgtgca acctgcgggg caaagcatgc    840

aaaaagctcc cctctaaggg gatgatatgt gtgactctca ataggcgtac tggttttgct    900

gccagaagct tccgctagtg tgaccaatac atttagagtt tgccattacc actggtgtta    960

aggacctccg taaagagctt ttggaaggcg gcagttcgag caagcaggag ctggactgcc   1020

tttaacagcc attggcaagt gaaaccatcg aatcactgtt actcacacag acgggcattt   1080

gctcgcactt ttttggttag ggcctcaagg gaatttgggg cagcagtgga ttagcacctc   1140
```

-continued

```
cactgctctt ttcgccaatt cttccgtcac cccgggttta caaacgaacg agctcgtagc   1200
tgtagtcccc ggcgtttgta ctgtgccccg cagtaagtgg gacgcactaa ggtcctccta   1260
ctttaacagt tcgagttcct tcttctcgcg ctcggctttc cgctctcgca tgtatcttgc   1320
accactgcaa ctgcaacatt cagtgactta gccgtcagat ggcatctgca gtgctgttgt   1380
cattaataaa tttcatcgtt gctgtacata gcctgtttat cacgcgacta tattgctaaa   1440
cgatgcaaag acagaagtgc cagcagcagc agaagcagcc taaacggcgc aaaccctgtc   1500
gggtggcagc ccgttaattt cgaagcatag tcatgcgtgc ttgcagcact tcagacactc   1560
aaaaaaataa tgcatatctc cacacaaatg caggcatatt ctcaacgtct cagtaggttg   1620
ctatgacctg aactgtgggg ggtggttgtt atacagaagg cgacgtaaac gaagtcctgc   1680
ggggactgaa caataatcta cggatgtatt tagtcctaaa agcacaaact tgatggcagt   1740
tggcagaaga aacatttaaa gaattagttt taaccaaaag gctacgagcg agggaggagg   1800
cgcggggatg ctgcagcacc tcctctacca ccctgtgtac ttccgtacgt tgcacaggtg   1860
gcggtgaata acgtccgtcg gttctacttg catccttaag ctgttattaa agcgtaattt   1920
tgcaaaaaat taggatagag aataaaatat ttggaaaaca atggcgcttt atttgctgaa   1980
acaacaagcg aggctggggg tcggctgttc gcccgggcgc gggctagcag gctagctgcg   2040
cagagactgc atgttccccc actgtacgtg cagggtgcgc gtgttgttgt tcgtgatggt   2100
atcggcgcgc gtatgtctca catccgttat ttagaggcta caacgagact gtctgttgtg   2160
tctgttccat agaaaaccaa aatgtctggc cgaggaaaag gaggaaaggg gttgggaaag   2220
ggaggcgcca agcgccaccg caaggtgttg cgcgacaaca tccagggtat cccgcggatg   2280
cagaaaccgg tgtgtctggt cgtcgcgatg acccccaaga ggggcatcgg catcaacaac   2340
ggcctcccgt ggccccactt gaccacagat ttcaaacact ttcgtcgtgt gacaaaaacg   2400
acgcccgaag aagccagtcg cctgaacggg tggcttccca ggaaatttgc aaagacgggc   2460
gactctggac ttccctctcc atcagtcggc aagagattca acgccgttgt catgggacgg   2520
aaaaactggg aaagcatgcc tcgaaagttt agacccctcg tggacagatt gaacatcgtc   2580
gtttcctctt ccctcaaaga agaagacatt gcggcggaga agcctcaagc tgaaggccag   2640
cagcgcgtcc gagtctgtgc ttcactccca gcagctctca gccttctgga ggaagagtac   2700
aaggattctg tcgaccagat ttttgtcgtg ggaggagcgg gactgtacga ggcagcgctg   2760
tctctgggcg ttgcctctca cctgtacatc acgcgtgtag cccgcgagtt tccgtgcgac   2820
gttttcttcc ctgcgttccc cggagatgac attctttcaa acaaatcaac tgctgcgcag   2880
gctgcagctc ctgccgagtc tgtgttcgtt ccccttttgtc cggagctcgg aagagagaag   2940
gacaatgaag cgacgtatcg acccatcttc atttccaaga ccttctcaga caacggggta   3000
ccctacgact ttgtggttct cgagaagaga aggaagactg acgacgcagc cactgcggaa   3060
ccgagcaacg caatgagctc cttgacgtcc acgagggaga caactcccgt gcacgggttg   3120
caggctcctt cttcggccgc agccattgcc ccggtgttgg cgtggatgga cgaagaagac   3180
cggaaaaaac gcgagcaaaa ggaactgatt cgggccgttc cgcatgttca ctttagaggc   3240
catgaagaat tccagtacct tgatctcatt gccgacatta ttaacaatgg aaggacaatg   3300
gatgaccgaa cgggcgttgg tgtcatctcc aaattcggct gcactatgcg ctactcgctg   3360
gatcaggcct ttccacttct caccacaaag cgtgtgttct ggaaaggggt cctcgaagag   3420
ttgctgtggt tcattcgcgg cgacacgaac gcaaaccatc tttctgagaa gggcgtgaag   3480
atctgggaca agaatgtgac acgcgagttc ctcgattcgc gcaatctccc ccaccgagag   3540
```

-continued

```
gtcggagaca tcggcccggg ctacggcttc cagtggagac acttcggcgc ggcatacaaa   3600
gacatgcaca cagactacac agggcagggc gtcgaccagc tgaagaatgt gatccagatg   3660
ctgagaacga atccaacaga tcgtcgcatg ctcatgactg cctggaatcc tgcagcgctg   3720
gacgaaatgg cgctgccgcc ttgtcacttg ttgtgccagt tctacgtgaa cgaccagaag   3780
gagctgtcgt gcatcatgta tcagcggtcg tgcgatgtcg gcctcggcgt ccccttcaac   3840
atcgcttcct attcgctttt gacgctcatg gttgcacacg tctgcaacct aaaacctaag   3900
gagttcattc acttcatggg gaacacgcat gtctacacga accatgtcga ggctttaaaa   3960
gagcagctgc ggagagaacc gagaccgttc cccattgtga acatcctcaa caaggaacgc   4020
atcaaggaaa tcgacgattt caccgccgag gattttgagg tcgtgggcta cgtcccgcac   4080
ggacgaatcc agatggagat ggctgtcttg gatcctgtcg ccaccatggt gagcaagggc   4140
gaggagctgt tcaccggggt ggtgcccatc ctggtcgagc tggacggcga cgtaaacggc   4200
cacaagttca gcgtgtccgg cgagggcgag ggcgatgcca cctacggcaa gctgaccctg   4260
aagttcatct gcaccaccgg caagctgccc gtgccctggc ccaccctcgt gaccaccttc   4320
ggctacggcc tgcagtgctt cgcccgctac cccgaccaca tgaagcagca cgacttcttc   4380
aagtccgcca tgcccgaagg ctacgtccag gagcgcacca tcttcttcaa ggacgacggc   4440
aactacaaga cccgcgccga ggtgaagttc gagggcgaca ccctggtgaa ccgcatcgag   4500
ctgaagggca tcgacttcaa ggaggacggc aacatcctgg ggcacaagct ggagtacaac   4560
tacaacagcc acaacgtcta tatcatggcc gacaagcaga agaacggcat caaggtgaac   4620
ttcaagatcc gccacaacat cgaggacggc agcgtgcagc tcgccgacca ctaccagcag   4680
aacaccccca tcggcgacgg ccccgtgctg ctgcccgaca accactacct gagctaccag   4740
tccgccctga gcaaagaccc caacgagaag cgcgatcaca tggtcctgct ggagttcgtg   4800
accgccgccg ggatcactct cggcatggac gagctgtaca agaagcttag ccaaccggtc   4860
gccaccatgg tgagcaaggg cgaggagctg ttcaccgggg tggtgcccat cctggtcgag   4920
ctggacggcg acgtaaacgg ccacaagttc agcgtgtccg gcgagggcga gggcgatgcc   4980
acctacggca agctgaccct gaagttcatc tgcaccaccg gcaagctgcc cgtgccctgg   5040
cccaccctcg tgaccacctt cggctacggc ctgcagtgct tcgcccgcta ccccgaccac   5100
atgaagcagc acgacttctt caagtccgcc atgcccgaag gctacgtcca ggagcgcacc   5160
atcttcttca aggacgacgg caactacaag acccgcgccg aggtgaagtt cgagggcgac   5220
accctggtga accgcatcga gctgaagggc atcgacttca aggaggacgg caacatcctg   5280
gggcacaagc tggagtacaa ctacaacagc cacaacgtct atatcatggc cgacaagcag   5340
aagaacggca tcaaggtgaa cttcaagatc cgccacaaca tcgaggacgg cagcgtgcag   5400
ctcgccgacc actaccagca gaacaccccc atcggcgacg gccccgtgct gctgcccgac   5460
aaccactacc tgagctacca gtccgccctg agcaaagacc ccaacgagaa gcgcgatcac   5520
atggtcctgc tggagttcgt gaccgccgcc gggatcactc tcggcatgga cgagctgtac   5580
aagaagcttt aggcggccgc gtttgcagca gagtagttca tgacttgcga aacggcctct   5640
cgattaataa tacgctttgc cgcaacgtga agtaggcgtt attgtgtgct gcctgtcgct   5700
gagctcctgc atcgagcggc aaggggttca accgagcgca aattctgtgg aaatagctgg   5760
acaaaagcat ctgcgacggg tgggggcagg cgcagctagc tgttgctccc gacatcagtc   5820
atggaaatgc gtttcaggct aagcaagtag ctgcccgcct ggtgggaaga tgaggctagg   5880
aactgctatg tttgcccctc acttggcggt attgcagtgt agtacgtgca ttgtgaaccc   5940
```

-continued

```
agagaaatgt gctccgcgtg acgcagcgag gcacagggga acagcaagag gggccgttat   6000
tgctcagcgt gctggacccc cttgttcctt caaaccttac ttatgagggc ttacgcatcg   6060
cacctgatgg gtcggtgtag cgtgatcatt tcactgttca gtagtaggta tgggaggagt   6120
gtagttggca ggatgtagga gctttgcaag cggtggaacg gttgagatga gtagtgaaca   6180
gaggctttgc ccaatgtcgg atagtgagtg tttctcgagc acgaaacgtg caaggcaaca   6240
ggttactgta ggtttatgta gttggcaaga gtgggccttg cccagtattc ggtagtaagt   6300
gtcaagcacg acaccagatt gcgaagcaac aggtaattgt aggtttacgt atcgtacgtt   6360
tttcatggga gtgtgacgga aagttgtggg tagcagggtc cgggggagtc tgcggcaagc   6420
agttcaacag attgatggaa cagaaagatt aagaggcgga gtgtccgctg ttgctgtggg   6480
cagaaagagg gcggcgtaga gaggcattta gtggatgctt ttgaggagtt ctgggaggtc   6540
atcagtagtg gggaaggtct accgcaccgt ctggtcggcc tattagttaa tgcccacatg   6600
aggcgatctt ttggtggtgc gtgacggggt cagtcattgg atttggtatc tgccgctcca   6660
tttgtagcta ggagagcctc tgatgccgtg acatcttgct aggttcgcac tgtttccaca   6720
acgactactt tgtttggtca ttttcaccgt gaaagtatgt tcaccttgga gagagaaaat   6780
ttgagagagc tctgagttgt tggaacagcc caagtagctg actctcatag gatactacta   6840
aagccaaacg gcgcgttgta gcgctcatct gcagggattg atctttaaaa aaatgatctt   6900
ttaaggttca tgccatactt attgagttcg ctaggtgtca acttgtcgaa cacattcttg   6960
aggtgttgcg tatctgggcg ctcccagggg ttccatgtga agcaattgct tcacatggaa   7020
cccctgggag cgcccagata cgcaacacct caagaatgtg ttcgacaagt tgacacctag   7080
cgaactcaat aagtatggca tgaaccttaa aagatcattt ttttaaagat caatccctgc   7140
agatgagcgc tacaacgcgc cgtttggctt tagtagtatc ctatgagagt cagctacttg   7200
ggctgttcca acaactcaga gctctctcaa attttctctc tccaaggtga acatactttc   7260
acggtgaaaa tgaccaaaca aagtagtcgt tgtggaaaca gtgcgaacct agcaagatgt   7320
cacggcatca gaggctctcc tagctacaaa tggagcggca gataccaaat ccaatgactg   7380
accccgtcac gcaccaccaa aagatcgcct catgtgggca ttaactaata ggccgaccag   7440
acggtgcggt agaccttccc cactactgat gacctcccag aactcctcaa aagcatccac   7500
taaatgcctc tctacgccgc cctctttctg cccacagcaa cagcggacac tccgcctctt   7560
aatctttctg ttccatcaat ctgttgaact gcttgccgca gactcccccg gaccctgcta   7620
cccacaactt tccgtcacac tcccatgaaa aacgtacgat acgtaaacct acaattacct   7680
gttgcttcgc aatctggtgt cgtgcttgac acttactacc gaatactggg caaggcccac   7740
tcttgccaac tacataaacc tacagtaacc tgttgccttg cacgtttcgt gctcgagaaa   7800
cactcactat ccgacattgg gcaaagcctc tgttcactac tcatctcaac cgttccaccg   7860
cttgcaaagc tcctacatcc tgccaactac actcctccca tacctactac tgaacagtga   7920
aatgatcacg ctacaccgac ccatcaggtg cgatgcgtaa gccctcataa gtaaggtttg   7980
aaggaacaag ggggtccagc acgctgagca ataacggccc ctcttgctgt tcccctgtgc   8040
ctcgctgcgt cacgcggagc acatttctct gggttcacaa tgcacgtact acactgcaat   8100
accgccaagt gaggggcaaa catagcagtt cctagcctca tcttcccacc aggcgggcag   8160
ctacttgctt agcctgaaac gcatttccat gactgatgtc gggagcaaca gctagctgcg   8220
cctgccccca cccgtcgcag atgcttttgt ccagctattt ccacagaatt tgcgctcggt   8280
tgaacccctt gccgctcgat gcaggagctc agcgacaggc agcacacaat aacgcctact   8340
```

-continued

```
tcacgttgcg gcaaagcgta ttattaatcg agaggccgtt tcgcaagtca tgaactactc   8400
tgctgcaaac gcggccgcat ttgcggccgc ctactgaatg tcgccgctgt cggcccagta   8460
gtcgtcttcg tctgtgatgt cgataactgt atcggcttca ggtgtctcgg cagttgctgc   8520
tccggtatct tctccttcga actcgacctg ttctgcctcc tgtgcgccag cgccacctcc   8580
gccgctagtg aaggctgcaa caccaccacc tacagcagct atgagcaaca caccaccaac   8640
acctcctgcc actgcagctg ttgggaagcc gccgccttct tccttcttct cctcctcctc   8700
ttcgggttct gggcgttcgt gaccctcctc tggttttggc tggacggcag gagtttcggg   8760
ggcagcctca gactcctgct tgccctcttc ttcggtaccc tcaacaggct gctcaggtgt   8820
ctcctcaggc tgagtcacac cctcctcagg cttctcctca ggctcagtaa cctcctcctc   8880
aggtagctcc tcctcaggct tctcctcagg ctcagttaca ctctccccag gaagctcttc   8940
ttctgggggc tgcacttcgc cttctcctgt ttgctcgcct tcctcgccac ctgcttcacc   9000
agtttcgcct tcgcctgtct cggtctctcc ctctccttcg cctgtttccg taccgggggc   9060
tggaatgggg tgcaattcca tggtggcgac aggatcccgg gcccgcggga taccctggat   9120
gttgtcgcgc aacaccttgc ggtggcgctt ggcgcctccc tttcccaacc cctttcctcc   9180
ttttcctcgg ccagacattt tggttttcta tggaacagac acaacagaca gtctcgttgt   9240
agcctctaaa taacggatgt gagacatacg cgcgccgata ccatcacgaa caacaacacg   9300
cgcaccctgc acgtacagtg ggggaacatg cagtctctgc gcagctagcc tgctagcccg   9360
cgcccgggcg aacagccgac ccccagcctc gcttgttgtt tcagcaaata aagcgccatt   9420
gttttccaaa tattttattc tctatcctaa ttttttgcaa aattacgctt taataacagc   9480
ttaaggatgc aagtagaacc gacggacgtt attcaccgcc acctgtgcaa cgtacggaag   9540
tacacagggt ggtagaggag gtgctgcagc atccccgcgc ctcctccctc gctcgtagcc   9600
ttttggttaa aactaattct ttaaatgttt cttctgccaa ctgccatcaa gtttgtgctt   9660
ttaggactaa atacatccgt agattattgt tcagtccccg caggacttcg tttacgtcgc   9720
cttctgtata acaaccaccc cccacagttc aggtcatagc aacctactga gacgttgaga   9780
atatgcctgc atttgtgtgg agatatgcat tatttttttg agtgtctgaa gtgctgcaag   9840
cacgcatgac tatgcttcga aattaacggg ctgccacccg acagggtttg cgccgtttag   9900
gctgcttctg ctgctgctgg cacttctgtc tttgcatcgt ttagcaatat agtcgcgtga   9960
taaacaggct atgtacagca acgatgaaat ttattaatga caacagcact gcagatgcca  10020
tctgacggct aagtcactga atgttgcagt tgcagtggtg caagatacat gcgagagcgg  10080
aaagccgagc gcgagaagaa ggaactcgaa ctgttaaagt aggaggacct tagtgcgtcc  10140
cacttactgc ggggcacagt acaaacgccg gggactacag ctacgagctc gttcgtttgt  10200
aaacccgggg tgacggaaga attggcgaaa agagcagtgg aggtgctaat ccactgctgc  10260
cccaaattcc cttgaggccc taaccaaaaa agtgcgagca aatgcccgtc tgtgtgagta  10320
acagtgattc gatggtttca cttgccaatg gctgttaaag gcagtccagc tcctgcttgc  10380
tcgaactgcc gccttccaaa agctctttac ggaggtcctt aacaccagtg gtaatggcaa  10440
actctaaatg tattggtcac actagcggaa gcttctggca gcaaaaccag tacgcctatt  10500
gagagtcaca cacatcccct tagaggggag ctttttgcat gctttgcccc gcaggttgca  10560
cagcattttg catgatgcat gcttttccca gtagagagtt cagctgcagc agcatcagct  10620
gcatgggctt tatatgcttc tgtaactgct gctgttgcgt ggctttgaaa acaacagggc  10680
tgggtattca aatactcact agaacgctgc tgttacgata tcatcaactg cgcgagcaac  10740
```

-continued

```
tatttggaaa ggaagagggc gggacattca agcacatcct agaatgctgt tgtagagata  10800
ttatcacctg ggggagcagc tatttgtgcc gctgtttttt tctgcaacta accgcagcga  10860
atgggcaaag cagccacaat gagtcgagca tcagccgttt cgcggcggat ggctcaccac  10920
gacagcaata gcgggttcta taagaattta aaaaacagaa aaagcaacag agtctccaac  10980
aatggaccaa tagatgtcag cagagcaaac agaaaccgcg aatgattcag ttttacagaa  11040
gctatgtatc tcgagtgtaa caagttcgtt cttgtgcctg tcactgacgg tgacaaaggt  11100
aacattgcta acctctactg ttgctacctt tgctggttca taaacttgtt tattgcagct  11160
tataatggtt acaaataaag caatagcatc acaaatttca caaataaagc atttttttca  11220
ctgcattcta gttgtggttt gtccaaactc atcaatgtat cttaaggcgt aaattgtaag  11280
cgttaatatt ttgttaaaat tcgcgttaaa tttttgttaa atcagctcat tttttaacca  11340
ataggccgaa atcggcaaaa tcccttataa atcaaaagaa tagaccgaga tagggttgag  11400
tgttgttcca gtttggaaca agagtccact attaaagaac gtggactcca acgtcaaagg  11460
gcgaaaaacc gtctatcagg gcgatggccc actacgtgaa ccatcaccct aatcaagttt  11520
tttggggtcg aggtgccgta aagcactaaa tcggaaccct aaagggagcc cccgatttag  11580
agcttgacgg ggaaagccgg cgaacgtggc gagaaaggaa gggaagaaag cgaaaggagc  11640
gggcgctagg gcgctggcaa gtgtagcggt cacgctgcgc gtaaccacca cacccgccgc  11700
gcttaatgcg ccgctacagg gcgcgtcagg tggcactttt cggggaaatg tgcgcggaac  11760
ccctatttgt ttatttttct aaatacattc aaatatgtat ccgctcatga gacaataacc  11820
ctgataaatg cttcaataat attgaaaaag gaagagtcct gaggcggaaa gaaccagctg  11880
tggaatgtgt gtcagttagg gtgtggaaag tccccaggct ccccagcagg cagaagtatg  11940
caaagcatgc atctcaatta gtcagcaacc aggtgtggaa agtccccagg ctccccagca  12000
ggcagaagta tgcaaagcat gcatctcaat tagtcagcaa ccatagtccc gcccctaact  12060
ccgcccatcc cgcccctaac tccgcccagt tccgcccatt ctccgcccca tggctgacta  12120
atttttttta tttatgcaga ggccgaggcc gcctcggcct ctgagctatt ccagaagtag  12180
tgaggaggct tttttggagg cctaggcttt tgcaaagatc gatcaagaga caggatgagg  12240
atcgtttcgc atgattgaac aagatggatt gcacgcaggt tctccggccg cttgggtgga  12300
gaggctattc ggctatgact gggcacaaca gacaatcggc tgctctgatg ccgccgtgtt  12360
ccggctgtca gcgcaggggc gcccggttct ttttgtcaag accgacctgt ccggtgccct  12420
gaatgaactg caagacgagg cagcgcggct atcgtggctg gccacgacgg gcgttccttg  12480
cgcagctgtg ctcgacgttg tcactgaagc gggaagggac tggctgctat tgggcgaagt  12540
gccggggcag gatctcctgt catctcacct tgctcctgcc gagaaagtat ccatcatggc  12600
tgatgcaatg cggcggctgc atacgcttga tccggctacc tgcccattcg accaccaagc  12660
gaaacatcgc atcgagcgag cacgtactcg gatggaagcc ggtcttgtcg atcaggatga  12720
tctggacgaa gagcatcagg ggctcgcgcc agccgaactg ttcgccaggc tcaaggcgag  12780
catgcccgac ggcgaggatc tcgtcgtgac ccatggcgat gcctgcttgc cgaatatcat  12840
ggtggaaaat ggccgctttt ctggattcat cgactgtggc cggctgggtg tggcggaccg  12900
ctatcaggac atagcgttgg ctacccgtga tattgctgaa gagcttggcg gcgaatgggc  12960
tgaccgcttc ctcgtgcttt acggtatcgc cgctcccgat tcgcagcgca tcgccttcta  13020
tcgccttctt gacgagttct tctgagcggg actctggggt tcgaaatgac cgaccaagcg  13080
acgcccaacc tgccatcacg agatttcgat tccaccgccg ccttctatga aaggttgggc  13140
```

```
ttcggaatcg ttttccggga cgccggctgg atgatcctcc agcgcgggga tctcatgctg  13200

gagttcttcg cccaccctag gggaggcta actgaaacac ggaaggagac aataccggaa  13260

ggaacccgcg ctatgacggc aataaaaaga cagaataaaa cgcacggtgt tgggtcgttt  13320

gttcataaac gcggggttcg gtcccagggc tggcactctg tcgatacccc accgagaccc  13380

cattggggcc aatacgcccg cgtttcttcc ttttccccac cccacccccc aagttcgggt  13440

gaaggcccag ggctcgcagc caacgtcggg gcggcaggcc ctgccatagc ctcaggttac  13500

tcatatatac tttagattga tttaaaactt catttttaat ttaaaaggat ctaggtgaag  13560

atcctttttg ataatctcat gaccaaaatc ccttaacgtg agttttcgtt ccactgagcg  13620

tcagaccccg tagaaaagat caaaggatct tcttgagatc cttttttct gcgcgtaatc  13680

tgctgcttgc aaacaaaaaa accaccgcta ccagcggtgg tttgtttgcc ggatcaagag  13740

ctaccaactc tttttccgaa ggtaactggc ttcagcagag cgcagatacc aaatactgtc  13800

cttctagtgt agccgtagtt aggccaccac ttcaagaact ctgtagcacc gcctacatac  13860

ctcgctctgc taatcctgtt accagtggct gctgccagtg gcgataagtc gtgtcttacc  13920

gggttggact caagacgata gttaccggat aaggcgcagc ggtcgggctg aacggggggt  13980

tcgtgcacac agcccagctt ggagcgaacg acctacaccg aactgagata cctacagcgt  14040

gagctatgag aaagcgccac gcttcccgaa gggagaaagg cggacaggta tccggtaagc  14100

ggcagggtcg gaacaggaga gcgcacgagg gagcttccag ggggaaacgc ctggtatctt  14160

tatagtcctg tcgggtttcg ccacctctga cttgagcgtc gatttttgtg atgctcgtca  14220

gggggcgga gcctatggaa aaacgccagc aacgcggcct ttttacggtt cctggccttt  14280

tgctggcctt ttgctcacat gttctttcct gcgttatccc ctgattctgt ggataaccgt  14340

attaccgcca tgcat                                                  14355
```

<210> SEQ ID NO 2
<211> LENGTH: 8654
<212> TYPE: DNA
<213> ORGANISM: Artificial Sequence
<220> FEATURE:
<223> OTHER INFORMATION: Sequence of expression vector pH4sp-HA1-EYFP-ACTIN

<400> SEQUENCE: 2

```
tagttattaa tagtaatcaa ttacggggtc attagttcat agcccatata tggagttccg    60

cgttacataa cttacggtaa atggcccgcc tggctgaccg cccaacgacc cccgcccatt   120

gacgtcaata atgacgtatg ttcccatagt aacgccaata gggactttcc attgacgtca   180

atgggtggag tatttacggt aaactgccca cttggcagta catcaagtgt atcatatgaa   240

ccagcaaagg tagcaacagt agaggttagc aatgttacct ttgtcaccgt cagtgacagg   300

cacaagaacg aacttgttac actcgagata catagcttct gtaaaactga atcattcgcg   360

gtttctgttt gctctgctga catctattgg tccattgttg gagactctgt tgctttttct   420

gtttttttaaa ttcttataga acccgctatt gctgtcgtgg tgagccatcc gccgcgaaac   480

ggctgatgct cgactcattg tggctgcttt gcccattcgc tgcggttagt tgcagaaaaa   540

aacagcggca caaatagctg ctcccccagg tgataatatc tctacaacag cattctagga   600

tgtgcttgaa tgtcccgccc tcttcctttc caaatagttg ctcgcgcagt tgatgatatc   660

gtaacagcag cgttctagtg agtatttgaa tacccagccc tgttgttttc aaagccacgc   720

aacagcagca gttacagaag catataaagc ccatgcagct gatgctgctg cagctgaact   780

ctctactggg aaaagcatgc atcatgcaaa atgctgtgca acctgcgggg caaagcatgc   840
```

-continued

```
aaaaagctcc cctctaaggg gatgtgtgtg actctcaata ggcgtactgg ttttgctgcc    900
agaagcttcc gctagtgtga ccaatacatt tagagtttgc cattaccact ggtgttaagg    960
acctccgtaa agagcttttg gaaggcggca gttcgagcaa gcaggagctg gactgccttt   1020
aacagccatt ggcaagtgaa accatcgaat cactgttact cacacagacg ggcatttgct   1080
cgcacttttt tggttagggc ctcaagggaa tttggggcag cagtggatta gcacctccac   1140
tgctcttttc gccaattctt ccgtcacccc gggtttacaa acgaacgagc tcgtagctgt   1200
agtccccggc gtttgtactg tgccccgcag taagtgggac gcactaaggt cctcctactt   1260
taacagttcg agttccttct tctcgcgctc ggctttccgc tctcgcatgt atcttgcacc   1320
actgcaactg caacattcag tgacttagcc gtcagatggc atctgcagtg ctgttgtcat   1380
taataaattt catcgttgct gtacatagcc tgtttatcac gcgactatat tgctaaacga   1440
tgcaaagaca gaagtgccag cagcagcaga agcagcctaa acggcgcaaa ccctgtcggg   1500
tggcagcccg ttaatttcga agcatagtca tgcgtgcttg cagcacttca gacactcaaa   1560
aaaataatgc atatctccac acaaatgcag gcatattctc aacgtctcag taggttgcta   1620
tgacctgaac tgtgggggtg ggttgttata cagaaggcga cgtaaacgaa gtcctgcggg   1680
gactgaacaa taatctacgg atgtatttag tcctaaaagc acaaacttga tggcagttgg   1740
cagaagaaac atttaaagaa ttagttttaa ccaaaaggct acgagcgagg gaggaggcgc   1800
ggggatgctg cagcacctcc tctaccaccc tgtgtacttc cgtacgttgc acaggtggcg   1860
gtgaataacg tccgtcggtt ctacttgcat ccttaagctg ttattaaagc gtaattttgc   1920
aaaaaattag gatagagaat aaaatatttg gaaaacaatg gcgctttatt tgctgaaaca   1980
acaagcgagg ctgggggtcg gctgttcgcc cgggcgcggg ctagcaggct agctgcgcag   2040
agactgcatg ttcccccact gtacgtgcag ggtgcgcgtg ttgttgttcg tgatggtatc   2100
ggcgcgcgta tgtctcacat ccgttattta gaggctacaa cgagactgtc tgttgtgtct   2160
gttccataga aaaccaaaat ggctcgtctt tcttttgttt ctcttctttc tctgtcactg   2220
ctcttcgggc agcaagcagt cagagctcag aattacccgc gggagaaaat agtgcttctt   2280
cttgcaatag tcagtcttgt taaaagtgat cagatttgca ttggttacca tgcaaacaac   2340
tcgacagagc aggttgacac aataatggaa aagaacgtca ctgttacaca cgcccaagac   2400
atactggaaa agacacacaa cgggaagctc tgcgatctag atggagtgaa gcctctaatt   2460
ttaagagatt gtagtgtagc tggatggctc ctcgggaacc caatgtgtga cgaattcctc   2520
aatgtgccgg aatggtctta catagtggag aagatcaatc cagccaatga cctctgttac   2580
ccagggaatt tcaacgacta tgaagaactg aaacacctat tgagcagaat aaaccatttt   2640
gagaaaattc agatcatccc caaaagttct tggtcagatc atgaagcctc gtcaggggtg   2700
agctcagcat gtccatacca gggaaggtcc tcctttttta gaaatgtggt atggcttatc   2760
aaaaagaaca atgcataccc aacaataaag agaagttaca ataataccaa ccaagaagat   2820
cttttggtac tgtgggggat tcaccatcca aatgatgcgg cagagcagac aaggctctat   2880
caaaacccaa ccacctatat ttccgttggg acatcaacac taaaccagag actggtacca   2940
aaaatagcta ctagatccaa ggtaaacggg caaagtggaa ggatggagtt cttttggaca   3000
attttaaaac cgaatgatgc aataaacttt gagagtaatg gaaatttcat tgctccagaa   3060
aatgcataca aaattgtcag gaaaggggac tcaacaatta tgaaaagtga attggaatat   3120
ggtaactgca acaccaagtg tcaaactcca ataggggcga taaactctag tatgccattc   3180
cacaacatcc accctctcac catcggggaa tgccccaaat atgtgaaatc aaacagatta   3240
```

-continued

```
atccttgcga ctgggctcag aaatagccct caaggagagg ggatccaagg aatggtgagc   3300
aagggcgagg agctgttcac cggggtggtg cccatcctgg tcgagctgga cggcgacgta   3360
aacggccaca agttcagcgt gtccggcgag ggcgagggcg atgccaccta cggcaagctg   3420
accctgaagt tcatctgcac caccggcaag ctgcccgtgc cctggcccac cctcgtgacc   3480
accttcggct acggcctgca gtgcttcgcc cgctaccccg accacatgaa gcagcacgac   3540
ttcttcaagt ccgccatgcc cgaaggctac gtccaggagc gcaccatctt cttcaaggac   3600
gacggcaact acaagacccg cgccgaggtg aagttcgagg gcgacaccct ggtgaaccgc   3660
atcgagctga agggcatcga cttcaaggag gacggcaaca tcctggggca caagctggag   3720
tacaactaca acagccacaa cgtctatatc atggccgaca agcagaagaa cggcatcaag   3780
gtgaacttca agatccgcca caacatcgag gacggcagcg tgcagctcgc cgaccactac   3840
cagcagaaca cccccatcgg cgacggcccc gtgctgctgc ccgacaacca ctacctgagc   3900
taccagtccg ccctgagcaa agaccccaac gagaagcgcg atcacatggt cctgctggag   3960
ttcgtgaccg ccgccgggat cactctcggc atggacgagc tgtacaagaa gctttaggcg   4020
gccgcgtttg cagcagagta gttcatgact tgcgaaacgg cctctcgatt aataatacgc   4080
tttgccgcaa cgtgaagtag gcgttattgt gtgctgcctg tcgctgagct cctgcatcga   4140
gcggcaaggg gttcaaccga gcgcaaattc tgtggaaata gctggacaaa agcatctgcg   4200
acgggtgggg gcaggcgcag ctagctgttg ctcccgacat cagtcatgga aatgcgtttc   4260
aggctaagca agtagctgcc cgcctggtgg gaagatgagg ctaggaactg ctatgtttgc   4320
ccctcacttg gcggtattgc agtgtagtac gtgcattgtg aacccagaga aatgtgctcc   4380
gcgtgacgca gcgaggcaca ggggaacagc aagaggggcc gttattgctc agcgtgctgg   4440
accccccttgt tccttcaaac cttacttatg agggcttacg catcgcacct gatgggtcgg   4500
tgtagcgtga tcatttcact gttcagtagt aggtatggga ggagtgtagt tggcaggatg   4560
taggagcttt gcaagcggtg gaacggttga gatgagtagt gaacagaggc tttgcccaat   4620
gtcggatagt gagtgtttct cgagcacgaa acgtgcaagg caacaggtta ctgtaggttt   4680
atgtagttgg caagagtggg ccttgcccag tattcggtag taagtgtcaa gcacgacacc   4740
agattgcgaa gcaacaggta attgtaggtt tacgtatcgt acgtttttca tgggagtgtg   4800
acggaaagtt gtgggtagca gggtccgggg gagtctgcgg caagcagttc aacagattga   4860
tggaacagaa agattaagag gcggagtgtc cgctgttgct gtgggcagaa agagggcggc   4920
gtagagaggc atttagtgga tgcttttgag gagttctggg aggtcatcag tagtggggaa   4980
ggtctaccgc accgtctggt cggcctatta gttaatgccc acatgaggcg atcttttggt   5040
ggtgcgtgac ggggtcagtc attggatttg gtatctgccg ctccatttgt agctaggaga   5100
gcctctgatg ccgtgacatc ttgctaggtt cgcactgttt ccacaacgac tactttgttt   5160
ggtcattttc accgtgaaag tatgttcacc ttggagagag aaaatttgag agagctctga   5220
gttgttggaa cagcccaagt agctgactct cataggatac tactaaagcc aaacggcgcg   5280
ttgtagcgct catctgcagg gattgatctt taaaaaaatg atcttttaag gttcatgcca   5340
tacttattga gttcgctagg tgtcaacttg tcgaacacat tcttgaggtg ttgcgtatct   5400
gggcgctccc aggggttcca tgtgaagcaa ttgttgttgt taacttgttt attgcagctt   5460
ataatggtta caaataaagc aatagcatca caaatttcac aaataaagca tttttttcac   5520
tgcattctag ttgtggtttg tccaaactca tcaatgtatc ttaaggcgta aattgtaagc   5580
gttaatattt tgttaaaatt cgcgttaaat ttttgttaaa tcagctcatt ttttaaccaa   5640
```

-continued

```
taggccgaaa tcggcaaaat cccttataaa tcaaaagaat agaccgagat agggttgagt   5700
gttgttccag tttggaacaa gagtccacta ttaaagaacg tggactccaa cgtcaaaggg   5760
cgaaaaaccg tctatcaggg cgatggccca ctacgtgaac catcacccta atcaagtttt   5820
ttggggtcga ggtgccgtaa agcactaaat cggaacccta aagggagccc ccgatttaga   5880
gcttgacggg gaaagccggc gaacgtggcg agaaaggaag ggaagaaagc gaaaggagcg   5940
ggcgctaggg cgctggcaag tgtagcggtc acgctgcgcg taaccaccac acccgccgcg   6000
cttaatgcgc cgctacaggg cgcgtcaggt ggcacttttc ggggaaatgt gcgcggaacc   6060
cctatttgtt tatttttcta aatacattca aatatgtatc cgctcatgag acaataaccc   6120
tgataaatgc ttcaataata ttgaaaaagg aagagtcctg aggcggaaag aaccagctgt   6180
ggaatgtgtg tcagttaggg tgtggaaagt ccccaggctc cccagcaggc agaagtatgc   6240
aaagcatgca tctcaattag tcagcaacca ggtgtggaaa gtccccaggc tccccagcag   6300
gcagaagtat gcaaagcatg catctcaatt agtcagcaac catagtcccg cccctaactc   6360
cgcccatccc gcccctaact ccgcccagtt ccgcccattc tccgccccat ggctgactaa   6420
ttttttttat ttatgcagag gccgaggccg cctcggcctc tgagctattc cagaagtagt   6480
gaggaggctt ttttggaggc ctaggctttt gcaaagatcg atcaagagac aggatgagga   6540
tcgtttcgca tgattgaaca agatggattg cacgcaggtt ctccggccgc ttgggtggag   6600
aggctattcg gctatgactg ggcacaacag acaatcggct gctctgatgc cgccgtgttc   6660
cggctgtcag cgcaggggcg cccggttctt tttgtcaaga ccgacctgtc cggtgccctg   6720
aatgaactgc aagacgaggc agcgcggcta tcgtggctgg ccacgacggg cgttccttgc   6780
gcagctgtgc tcgacgttgt cactgaagcg ggaagggact ggctgctatt gggcgaagtg   6840
ccggggcagg atctcctgtc atctcacctt gctcctgccg agaaagtatc catcatggct   6900
gatgcaatgc ggcggctgca tacgcttgat ccggctacct gcccattcga ccaccaagcg   6960
aaacatcgca tcgagcgagc acgtactcgg atggaagccg gtcttgtcga tcaggatgat   7020
ctggacgaag agcatcaggg gctcgcgcca gccgaactgt tcgccaggct caaggcgagc   7080
atgcccgacg gcgaggatct cgtcgtgacc catggcgatg cctgcttgcc gaatatcatg   7140
gtggaaaatg gccgcttttc tggattcatc gactgtggcc ggctgggtgt ggcggaccgc   7200
tatcaggaca tagcgttggc tacccgtgat attgctgaag agcttggcgg cgaatgggct   7260
gaccgcttcc tcgtgcttta cggtatcgcc gctcccgatt cgcagcgcat cgccttctat   7320
cgccttcttg acgagttctt ctgagcggga ctctggggtt cgaaatgacc gaccaagcga   7380
cgcccaacct gccatcacga gatttcgatt ccaccgccgc cttctatgaa aggttgggct   7440
tcggaatcgt tttccgggac gccggctgga tgatcctcca gcgcggggat ctcatgctgg   7500
agttcttcgc ccaccctagg gggaggctaa ctgaaacacg gaaggagaca ataccggaag   7560
gaacccgcgc tatgacggca ataaaaagac agaataaaac gcacggtgtt gggtcgtttg   7620
ttcataaacg cggggttcgg tcccagggct ggcactctgt cgataccccca ccgagacccc   7680
attggggcca atacgcccgc gtttcttcct tttccccacc ccaccccccca agttcgggtg   7740
aaggcccagg gctcgcagcc aacgtcgggg cggcaggccc tgccatagcc tcaggttact   7800
catatatact ttagattgat ttaaaacttc atttttaatt taaaaggatc taggtgaaga   7860
tcctttttga taatctcatg accaaaatcc cttaacgtga gttttcgttc cactgagcgt   7920
cagaccccgt agaaaagatc aaaggatctt cttgagatcc tttttttctg cgcgtaatct   7980
gctgcttgca aacaaaaaaa ccaccgctac cagcggtggt ttgtttgccg gatcaagagc   8040
```

```
taccaactct ttttccgaag gtaactggct tcagcagagc gcagatacca aatactgtcc   8100

ttctagtgta gccgtagtta ggccaccact tcaagaactc tgtagcaccg cctacatacc   8160

tcgctctgct aatcctgtta ccagtggctg ctgccagtgg cgataagtcg tgtcttaccg   8220

ggttggactc aagacgatag ttaccggata aggcgcagcg gtcgggctga acggggggtt   8280

cgtgcacaca gcccagcttg gagcgaacga cctacaccga actgagatac ctacagcgtg   8340

agctatgaga aagcgccacg cttcccgaag ggagaaaggc ggacaggtat ccggtaagcg   8400

gcagggtcgg aacaggagag cgcacgaggg agcttccagg gggaaacgcc tggtatcttt   8460

atagtcctgt cgggtttcgc cacctctgac ttgagcgtcg atttttgtga tgctcgtcag   8520

gggggcggag cctatggaaa aacgccagca acgcggcctt tttacggttc ctggcctttt   8580

gctggccttt tgctcacatg ttctttcctg cgttatcccc tgattctgtg gataaccgta   8640

ttaccgccat gcat                                                     8654
```

<210> SEQ ID NO 3
<211> LENGTH: 7694
<212> TYPE: DNA
<213> ORGANISM: Artificial Sequence
<220> FEATURE:
<223> OTHER INFORMATION: Sequence of expression vector pH4SP-M2e-EYFP-ACTIN

<400> SEQUENCE: 3

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgaa    240

ccagcaaagg tagcaacagt agaggttagc aatgttacct ttgtcaccgt cagtgacagg    300

cacaagaacg aacttgttac actcgagata catagcttct gtaaaactga atcattcgcg    360

gtttctgttt gctctgctga catctattgg tccattgttg gagactctgt tgctttttct    420

gtttttttaaa ttcttataga acccgctatt gctgtcgtgg tgagccatcc gccgcgaaac    480

ggctgatgct cgactcattg tggctgcttt gcccattcgc tgcggttagt tgcagaaaaa    540

aacagcggca caaatagctg ctcccccagg tgataatatc tctacaacag cattctagga    600

tgtgcttgaa tgtcccgccc tcttcctttc caaatagttg ctcgcgcagt tgatgatatc    660

gtaacagcag cgttctagtg agtatttgaa tacccagccc tgttgttttc aaagccacgc    720

aacagcagca gttacagaag catataaagc ccatgcagct gatgctgctg cagctgaact    780

ctctactggg aaaagcatgc atcatgcaaa atgctgtgca acctgcgggg caaagcatgc    840

aaaaagctcc cctctaaggg gatgtgtgtg actctcaata ggcgtactgg ttttgctgcc    900

agaagcttcc gctagtgtga ccaatacatt tagagtttgc cattaccact ggtgttaagg    960

acctccgtaa agagcttttg gaaggcggca gttcgagcaa gcaggagctg gactgccttt   1020

aacagccatt ggcaagtgaa accatcgaat cactgttact cacacagacg ggcatttgct   1080

cgcacttttt tggttagggc ctcaagggaa tttggggcag cagtggatta gcacctccac   1140

tgctcttttc gccaattctt ccgtcacccc gggtttacaa acgaacgagc tcgtagctgt   1200

agtccccggc gtttgtactg tgccccgcag taagtgggac gcactaaggt cctcctactt   1260

taacagttcg agttccttct tctcgcgctc ggctttccgc tctcgcatgt atcttgcacc   1320

actgcaactg caacattcag tgacttagcc gtcagatggc atctgcagtg ctgttgtcat   1380
```

-continued

```
taataaattt catcgttgct gtacatagcc tgtttatcac gcgactatat tgctaaacga   1440
tgcaaagaca gaagtgccag cagcagcaga agcagcctaa acggcgcaaa ccctgtcggg   1500
tggcagcccg ttaatttcga agcatagtca tgcgtgcttg cagcacttca gacactcaaa   1560
aaaataatgc atatctccac acaaatgcag gcatattctc aacgtctcag taggttgcta   1620
tgacctgaac tgtggggggt ggttgttata cagaaggcga cgtaaacgaa gtcctgcggg   1680
gactgaacaa taatctacgg atgtatttag tcctaaaagc acaaacttga tggcagttgg   1740
cagaagaaac atttaaagaa ttagttttaa ccaaaaggct acgagcgagg gaggaggcgc   1800
ggggatgctg cagcacctcc tctaccaccc tgtgtacttc cgtacgttgc acaggtggcg   1860
gtgaataacg tccgtcggtt ctacttgcat ccttaagctg ttattaaagc gtaattttgc   1920
aaaaaattag gatagagaat aaaatatttg gaaaacaatg gcgctttatt tgctgaaaca   1980
acaagcgagg ctgggggtcg gctgttcgcc cgggcgcggg ctagcaggct agctgcgcag   2040
agactgcatg ttccccccact gtacgtgcag ggtgcgcgtg ttgttgttcg tgatggtatc   2100
ggcgcgcgta tgtctcacat ccgttattta gaggctacaa cgagactgtc tgttgtgtct   2160
gttccataga aaaccaaaat ggctcgtctt tcttttgttt ctcttctttc tctgtcactg   2220
ctcttcgggc agcaagcagt cagagctcag aattacccgc ggagtcttct aaccgaggtc   2280
gaaacgccta ccagaaacga atgggagtgc agatgcagcg attcaagtga tatggtgagc   2340
aagggcgagg agctgttcac cggggtggtg cccatcctgg tcgagctgga cggcgacgta   2400
aacggccaca agttcagcgt gtccggcgag ggcgagggcg atgccaccta cggcaagctg   2460
accctgaagt tcatctgcac caccggcaag ctgcccgtgc cctggcccac cctcgtgacc   2520
accttcggct acggcctgca gtgcttcgcc cgctaccccg accacatgaa gcagcacgac   2580
ttcttcaagt ccgccatgcc cgaaggctac gtccaggagc gcaccatctt cttcaaggac   2640
gacggcaact acaagacccg cgccgaggtg aagttcgagg gcgacaccct ggtgaaccgc   2700
atcgagctga agggcatcga cttcaaggag gacggcaaca tcctggggca caagctggag   2760
tacaactaca acagccacaa cgtctatatc atggccgaca agcagaagaa cggcatcaag   2820
gtgaacttca agatccgcca caacatcgag gacggcagcg tgcagctcgc cgaccactac   2880
cagcagaaca cccccatcgg cgacggcccc gtgctgctgc ccgacaacca ctacctgagc   2940
taccagtccg ccctgagcaa agaccccaac gagaagcgcg atcacatggt cctgctggag   3000
ttcgtgaccg ccgccgggat cactctcggc atggacgagc tgtacaagaa gctttaggcg   3060
gccgcgtttg cagcagagta gttcatgact tgcgaaacgg cctctcgatt aataatacgc   3120
tttgccgcaa cgtgaagtag gcgttattgt gtgctgcctg tcgctgagct cctgcatcga   3180
gcggcaaggg gttcaaccga gcgcaaattc tgtggaaata gctggacaaa agcatctgcg   3240
acgggtgggg gcaggcgcag ctagctgttg ctcccgacat cagtcatgga aatgcgtttc   3300
aggctaagca agtagctgcc cgcctggtgg gaagatgagg ctaggaactg ctatgtttgc   3360
ccctcacttg gcggtattgc agtgtagtac gtgcattgtg aacccagaga aatgtgctcc   3420
gcgtgacgca gcgaggcaca ggggaacagc aagaggggcc gttattgctc agcgtgctgg   3480
accccttgt tccttcaaac cttacttatg agggcttacg catcgcacct gatgggtcgg   3540
tgtagcgtga tcatttcact gttcagtagt aggtatggga ggagtgtagt tggcaggatg   3600
taggagcttt gcaagcggtg gaacggttga gatgagtagt gaacagaggc tttgcccaat   3660
gtcggatagt gagtgtttct cgagcacgaa acgtgcaagg caacaggtta ctgtaggttt   3720
atgtagttgg caagagtggg ccttgcccag tattcggtag taagtgtcaa gcacgacacc   3780
```

-continued

```
agattgcgaa gcaacaggta attgtaggtt tacgtatcgt acgtttttca tgggagtgtg   3840
acggaaagtt gtgggtagca gggtccgggg gagtctgcgg caagcagttc aacagattga   3900
tggaacagaa agattaagag gcggagtgtc cgctgttgct gtgggcagaa agagggcggc   3960
gtagagaggc atttagtgga tgcttttgag gagttctggg aggtcatcag tagtggggaa   4020
ggtctaccgc accgtctggt cggcctatta gttaatgccc acatgaggcg atcttttggt   4080
ggtgcgtgac ggggtcagtc attggatttg gtatctgccg ctccatttgt agctaggaga   4140
gcctctgatg ccgtgacatc ttgctaggtt cgcactgttt ccacaacgac tactttgttt   4200
ggtcattttc accgtgaaag tatgttcacc ttggagagag aaaatttgag agagctctga   4260
gttgttggaa cagcccaagt agctgactct cataggatac tactaaagcc aaacggcgcg   4320
ttgtagcgct catctgcagg gattgatctt taaaaaaatg atcttttaag gttcatgcca   4380
tacttattga gttcgctagg tgtcaacttg tcgaacacat tcttgaggtg ttgcgtatct   4440
gggcgctccc aggggttcca tgtgaagcaa ttgttgttgt taacttgttt attgcagctt   4500
ataatggtta caaataaagc aatagcatca caaatttcac aaataaagca tttttttcac   4560
tgcattctag ttgtggtttg tccaaactca tcaatgtatc ttaaggcgta aattgtaagc   4620
gttaatattt tgttaaaatt cgcgttaaat ttttgttaaa tcagctcatt ttttaaccaa   4680
taggccgaaa tcggcaaaat cccttataaa tcaaaagaat agaccgagat agggttgagt   4740
gttgttccag tttggaacaa gagtccacta ttaaagaacg tggactccaa cgtcaaaggg   4800
cgaaaaaccg tctatcaggg cgatggccca ctacgtgaac catcacccta atcaagtttt   4860
ttggggtcga ggtgccgtaa agcactaaat cggaacccta aagggagccc ccgatttaga   4920
gcttgacggg gaaagccggc gaacgtggcg agaaaggaag ggaagaaagc gaaaggagcg   4980
ggcgctaggg cgctggcaag tgtagcggtc acgctgcgcg taaccaccac acccgccgcg   5040
cttaatgcgc cgctacaggg cgcgtcaggt ggcacttttc ggggaaatgt gcgcggaacc   5100
cctatttgtt tatttttcta aatacattca aatatgtatc cgctcatgag acaataaccc   5160
tgataaatgc ttcaataata ttgaaaaagg aagagtcctg aggcggaaag aaccagctgt   5220
ggaatgtgtg tcagttaggg tgtggaaagt ccccaggctc cccagcaggc agaagtatgc   5280
aaagcatgca tctcaattag tcagcaacca ggtgtggaaa gtccccaggc tccccagcag   5340
gcagaagtat gcaaagcatg catctcaatt agtcagcaac catagtcccg cccctaactc   5400
cgcccatccc gcccctaact ccgcccagtt ccgcccattc tccgccccat ggctgactaa   5460
ttttttttat ttatgcagag gccgaggccg cctcggcctc tgagctattc cagaagtagt   5520
gaggaggctt ttttggaggc ctaggctttt gcaaagatcg atcaagagac aggatgagga   5580
tcgtttcgca tgattgaaca agatggattg cacgcaggtt ctccggccgc ttgggtggag   5640
aggctattcg gctatgactg ggcacaacag acaatcggct gctctgatgc cgccgtgttc   5700
cggctgtcag cgcaggggcg cccggttctt tttgtcaaga ccgacctgtc cggtgccctg   5760
aatgaactgc aagacgaggc agcgcggcta tcgtggctgg ccacgacggg cgttccttgc   5820
gcagctgtgc tcgacgttgt cactgaagcg ggaagggact ggctgctatt gggcgaagtg   5880
ccggggcagg atctcctgtc atctcacctt gctcctgccg agaaagtatc catcatggct   5940
gatgcaatgc ggcggctgca tacgcttgat ccggctacct gcccattcga ccaccaagcg   6000
aaacatcgca tcgagcgagc acgtactcgg atggaagccg gtcttgtcga tcaggatgat   6060
ctggacgaag agcatcaggg gctcgcgcca gccgaactgt tcgccaggct caaggcgagc   6120
atgcccgacg gcgaggatct cgtcgtgacc catggcgatg cctgcttgcc gaatatcatg   6180
```

```
gtggaaaatg gccgcttttc tggattcatc gactgtggcc ggctgggtgt ggcggaccgc   6240

tatcaggaca tagcgttggc tacccgtgat attgctgaag agcttggcgg cgaatgggct   6300

gaccgcttcc tcgtgcttta cggtatcgcc gctcccgatt cgcagcgcat cgccttctat   6360

cgccttcttg acgagttctt ctgagcggga ctctggggtt cgaaatgacc gaccaagcga   6420

cgcccaacct gccatcacga gatttcgatt ccaccgccgc cttctatgaa aggttgggct   6480

tcggaatcgt tttccgggac gccggctgga tgatcctcca gcgcggggat ctcatgctgg   6540

agttcttcgc ccaccctagg gggaggctaa ctgaaacacg gaaggagaca ataccggaag   6600

gaacccgcgc tatgacggca ataaaaagac agaataaaac gcacggtgtt gggtcgtttg   6660

ttcataaacg cggggttcgg tcccagggct ggcactctgt cgatacccca ccgagacccc   6720

attggggcca atacgcccgc gtttcttcct tttccccacc ccacccccca agttcgggtg   6780

aaggcccagg gctcgcagcc aacgtcgggg cggcaggccc tgccatagcc tcaggttact   6840

catatatact ttagattgat ttaaaacttc atttttaatt taaaaggatc taggtgaaga   6900

tcctttttga taatctcatg accaaaatcc cttaacgtga gttttcgttc cactgagcgt   6960

cagaccccgt agaaaagatc aaaggatctt cttgagatcc tttttttctg cgcgtaatct   7020

gctgcttgca aacaaaaaaa ccaccgctac cagcggtggt ttgtttgccg gatcaagagc   7080

taccaactct ttttccgaag gtaactggct tcagcagagc gcagatacca aatactgtcc   7140

ttctagtgta gccgtagtta ggccaccact tcaagaactc tgtagcaccg cctacatacc   7200

tcgctctgct aatcctgtta ccagtggctg ctgccagtgg cgataagtcg tgtcttaccg   7260

ggttggactc aagacgatag ttaccggata aggcgcagcg gtcgggctga acggggggtt   7320

cgtgcacaca gcccagcttg gagcgaacga cctacaccga actgagatac ctacagcgtg   7380

agctatgaga aagcgccacg cttcccgaag ggagaaaggc ggacaggtat ccggtaagcg   7440

gcagggtcgg aacaggagag cgcacgaggg agcttccagg gggaaacgcc tggtatcttt   7500

atagtcctgt cgggtttcgc cacctctgac ttgagcgtcg atttttgtga tgctcgtcag   7560

gggggcggag cctatggaaa aacgccagca acgcggcctt tttacggttc ctggcctttt   7620

gctggccttt tgctcacatg ttctttcctg cgttatcccc tgattctgtg gataaccgta   7680

ttaccgccat gcat                                                     7694
```

```
<210> SEQ ID NO 4
<211> LENGTH: 9640
<212> TYPE: DNA
<213> ORGANISM: Artificial Sequence
<220> FEATURE:
<223> OTHER INFORMATION: Sequence of expression vector
      pHgra8-EYFP-HA-A3'

<400> SEQUENCE: 4

agatctaacc agcaaaggta gcaacagtag aggttagcaa tgttaccttt gtcaccgtca     60

gtgacaggca caagaacgaa cttgttacac tcgagataca tagcttctgt aaaactgaat    120

cattcgcggt ttctgtttgc tctgctgaca tctattggtc cattgttgga gactctgttg    180

ctttttctgt tttttaaatt cttatagaac ccgctattgc tgtcgtggtg agccatccgc    240

cgcgaaacgg ctgatgctcg actcattgtg gctgctttgc ccattcgctg cggttagttg    300

cagaaaaaaa cagcggcaca aatagctgct cccccaggtg ataaatatctc tacaacagca   360

ttctaggatg tgcttgaatg tcccgccctc ttcctttcca aatagttgct cgcgcagttg    420

atgatatcgt aacagcagcg ttctagtgag tatttgaata cccagccctg ttgttttcaa    480

agccacgcaa cagcagcagt tacagaagca tataaagccc atgcagctga tgctgctgca    540
```

```
gctgaactct ctactgggaa aagcatgcat catgcaaaat gctgtgcaac ctgcggggca    600
aagcatgcaa aaagctcccc tctaagggga tgtgtgtgac tctcaatagg cgtactggtt    660
ttgctgccag aagcttccgc tagtgtgacc aatacattta gagtttgcca ttaccactgg    720
tgttaaggac ctccgtaaag agcttttgga aggcggcagt tcgagcaagc aggagctgga    780
ctgcctttaa cagccattgg caagtgaaac catcgaatca ctgttactca cacagacggg    840
catttgctcg cactttttttg gttagggcct caagggaatt tggggcagca gtggattagc    900
acctccactg ctcttttcgc caattcttcc gtcaccccgg gtttacaaac gaacgagctc    960
gtagctgtag tccccggcgt ttgtactgtg ccccgcagta agtgggacgc actaaggtcc   1020
tcctacttta acagttcgag ttccttcttc tcgcgctcgg ctttccgctc tcgcatgtat   1080
cttgcaccac tgcaactgca acattcagtg acttagccgt cagatggcat ctgcagtgct   1140
gttgtcatta ataaatttca tcgttgctgt acatagcctg tttatcacgc gactatattg   1200
ctaaacgatg caaagacaga agtgccagca gcagcagaag cagcctaaac ggcgcaaacc   1260
ctgtcgggtg gcagcccgtt aatttcgaag catagtcatg cgtgcttgca gcacttcaga   1320
cactcaaaaa aataatgcat atctccacac aaatgcaggc atattctcaa cgtctcagta   1380
ggttgctatg acctgaactg tggggggtgg ttgttataca gaaggcgacg taaacgaagt   1440
cctgcgggga ctgaacaata atctacggat gtatttagtc ctaaaagcac aaacttgatg   1500
gcagttggca gaagaaacat ttaaagaatt agttttaacc aaaaggctac gagcgaggga   1560
ggaggcgcgg ggatgctgca gcacctcctc taccaccctg tgtacttccg tacgttgcac   1620
aggtggcggt gaataacgtc cgtcggttct acttgcatcc ttaagctgtt attaaagcgt   1680
aattttgcaa aaaattagga tagagaataa aatatttgga aaacaatggc gctttatttg   1740
ctgaaacaac aagcgaggct gggggtcggc tgttcgcccg ggcgcgggct agcaggctag   1800
ctgcgcagag actgcatgtt cccccactgt acgtgcaggg tgcgcgtgtt gttgttcgtg   1860
atggtatcgg cgcgcgtatg tctcacatcc gttatttaga ggctacaacg agactgtctg   1920
ttgtgtctgt tccatagaaa accaaaatgg ctttaccatt gcgtgtttcg gccacggtgt   1980
tcgtggtctt cgctgtcttt ggtgtagctc gcgccggtac cgtcgccacc atggtgagca   2040
agggcgagga gctgttcacc ggggtggtgc ccatcctggt cgagctggac ggcgacgtaa   2100
acggccacaa gttcagcgtg tccggcgagg gcgagggcga tgccacctac ggcaagctga   2160
ccctgaagtt catctgcacc accggcaagc tgcccgtgcc ctggcccacc ctcgtgacca   2220
ccttcggcta cggcctgcag tgcttcgccc gctaccccga ccacatgaag cagcacgact   2280
tcttcaagtc cgccatgccc gaaggctacg tccaggagcg caccatcttc ttcaaggacg   2340
acggcaacta caagacccgc gccgaggtga agttcgaggg cgacaccctg gtgaaccgca   2400
tcgagctgaa gggcatcgac ttcaaggagg acggcaacat cctggggcac aagctggagt   2460
acaactacaa cagccacaac gtctatatca tggccgacaa gcagaagaac ggcatcaagg   2520
tgaacttcaa gatccgccac aacatcgagg acggcagcgt gcagctcgcc gaccactacc   2580
agcagaacac ccccatcggc gacggccccg tgctgctgcc cgacaaccac tacctgagct   2640
accagtccgc cctgagcaaa gaccccaacg agaagcgcga tcacatggtc ctgctggagt   2700
tcgtgaccgc cgccgggatc actctcggca tggacgagct gtacaagaag cttagccaac   2760
cggtcgccac catggagaaa atagtgcttc ttcttgcaat agtcagtctt gttaaaagtg   2820
atcagatttg cattggttac catgcaaaca actcgacaga gcaggttgac acaataatgg   2880
aaaagaacgt cactgttaca cacgcccaag acatactgga aagacacac aacgggaagc   2940
```

```
tctgcgatct agatggagtg aagcctctaa ttttaagaga ttgtagtgta gctggatggc   3000
tcctcgggaa cccaatgtgt gacgaattcc tcaatgtgcc ggaatggtct tacatagtgg   3060
agaagatcaa tccagccaat gacctctgtt acccagggaa tttcaacgac tatgaagaac   3120
tgaaacacct attgagcaga ataaaccatt ttgagaaaat tcagatcatc cccaaaagtt   3180
cttggtcaga tcatgaagcc tcgtcagggg tgagctcagc atgtccatac cagggaaggt   3240
cctccttttt tagaaatgtg gtatggctta tcaaaaagaa caatgcatac ccaacaataa   3300
agagaagtta caataatacc aaccaagaag atcttttggt actgtggggg attcaccatc   3360
caaatgatgc ggcagagcag acaaggctct atcaaaaccc aaccacctat atttccgttg   3420
ggacatcaac actaaaccag agattggtac caaaaatagc tactagatcc aaggtaaacg   3480
ggcaaagtgg aaggatggag ttcttttgga caattttaaa accgaatgat gcaataaact   3540
ttgagagtaa tggaaatttc attgctccag aaaatgcata caaaattgtc aggaaagggg   3600
actcaacaat tatgaaaagt gaattggaat atggtaactg caacaccaag tgtcaaactc   3660
caataggggc gataaactct agtatgccat tccacaacat ccaccctctc accatcgggg   3720
aatgccccaa atatgtgaaa tcaaacagat taatccttgc gactgggctc agaaatagcc   3780
ctcaaggaga gagaagaagg aaaaagagag gactatttgg agctatagca ggttttatag   3840
agggaggatg gcagggaatg gtagatggtt ggtatgggta ccaccatagc aacgagcagg   3900
ggagtgggta cgctgcagac aaagaatcca ctcaaaaggc aatagatgga gtcaccaata   3960
aggtcaactc gatcattgac aaaatgaaca ctcagtttga ggccgttgga agggaattta   4020
ataacttaga aaggagaata gaaaatttaa acaagaagat ggaagacgga ttcctagatg   4080
tctggactta taatgctgaa cttctggttc tcatggaaaa tgagagaact ctagactttc   4140
atgactcaaa tgtcaagaac ctttacgaca aggtccgact acagcttagg gataatgcaa   4200
aggagcttgg taacggttgt ttcgagttct atcacagatg tgataatgaa tgtatggaaa   4260
gtgtaagaaa cggaacgtat gactacccgc agtattcaga agaagcaaga ttaaaaagag   4320
aggaaataag tggagtaaaa ttggaatcaa taggaactta ccaaatactg tcaatttatt   4380
caacagtggc gagctcccta gcactggcaa tcatggtggc tggtctatct ttatggatgt   4440
gctccaatgg atcgttacaa tgcagaattt gcatttaggc ggccgcggga attcgattgg   4500
ccgcgtttgc agcagagtag ttcatgactt gcgaaacggc ctctcgatta ataatacgct   4560
ttgccgcaac gtgaagtagg cgttattgtg tgctgcctgt cgctgagctc ctgcatcgag   4620
cggcaagggg ttcaaccgag cgcaaattct gtggaaatag ctggacaaaa gcatctgcga   4680
cgggtggggg caggcgcagc tagctgttgc tcccgacatc agtcatggaa atgcgtttca   4740
ggctaagcaa gtagctgccc gcctggtggg aagatgaggc taggaactgc tatgtttgcc   4800
cctcacttgg cggtattgca gtgtagtacg tgcattgtga acccagagaa atgtgctccg   4860
cgtgacgcag cgaggcacag gggaacagca agaggggccg ttattgctca gcgtgctgga   4920
ccccccttgtt ccttcaaacc ttacttatga gggcttacgc atcgcacctg atgggtcggt   4980
gtagcgtgat catttcactg ttcagtagta ggtatgggag gagtgtagtt ggcaggatgt   5040
aggagctttg caagcggtgg aacggttgag atgagtagtg aacagaggct ttgcccaatg   5100
tcggatagtg agtgtttctc gagcacgaaa cgtgcaaggc aacaggttac tgtaggttta   5160
tgtagttggc aagagtgggc cttgcccagt attcggtagt aagtgtcaag cacgacacca   5220
gattgcgaag caacaggtaa ttgtaggttt acgtatcgta cgtttttcat gggagtgtga   5280
cggaaagttg tgggtagcag ggtccggggg agtctgcggc aagcagttca acagattgat   5340
```

-continued

```
ggaacagaaa gattaagagg cggagtgtcc gctgttgctg tgggcagaaa gagggcggcg   5400
tagagaggca tttagtggat gcttttgagg agttctggga ggtcatcagt agtggggaag   5460
gtctaccgca ccgtctggtc ggcctattag ttaatgccca catgaggcga tcttttggtg   5520
gtgcgtgacg gggtcagtca ttggatttgg tatctgccgc tccatttgta gctaggagag   5580
cctctgatgc cgtgacatct tgctaggttc gcactgtttc cacaacgact actttgtttg   5640
gtcattttca ccgtgaaagt atgttcacct tggagagaga aaatttgaga gagctctgag   5700
ttgttggaac agcccaagta gctgactctc ataggatact actaaagcca aacggcgcgt   5760
tgtagcgctc atctgcaggg attgatcttt aaaaaaatga tcttttaagg ttcatgccat   5820
acttattgag ttcgctaggt gtcaacttgt cgaacacatt cttgaggtgt tgcgtatctg   5880
ggcgctccca ggggttccat gtgaagcaat tgtccagcgt tgcgcggacg ctcggatgaa   5940
accaggcagg aacggtaggt ttgcgacgat tgtacaagag cgcgtgtatt actcctacgc   6000
atccacagaa atcagcattg gtaatcgtcg tggctgttgc aaggtctggt agcaaagctg   6060
catatatttg cttgactgaa tttcacttac cctcgttaga gtgtatgtct tcgtagggta   6120
tcggaccccc cagtatttca attaggcagc atgcaagccc ccaaatatca agcttctcat   6180
ccacgtagtt gccttccacg aagcattcag gagccatgta gcggggagac cctccgttgt   6240
cctccaattt aagctttccg tgctgctcta atgaccgtgt cttgccaaag tcgcagagcc   6300
gaatgttgta ctgcacacat aagttgaaca tcacagagaa accaagggag aaattcactc   6360
acagggctgt gcccaccctc attcatcctg gtagaatagc caaccaattg cacccacgtg   6420
aagccaaaac gagcgaacat tcatgacagc aagttatgaa ttttggcgac ctgtgttggt   6480
aaaaatgaaa aggaggctac gaagaatttg agcgtttggt gcgaatcctg cttacatctc   6540
ggtcgcttaa ggcgtaaatt gtaagcgtta atattttgtt aaaattcgcg ttaaattttt   6600
gttaaatcag ctcatttttt aaccaatagg ccgaaatcgg caaaatccct tataaatcaa   6660
aagaatagac cgagataggg ttgagtgttg ttccagtttg gaacaagagt ccactattaa   6720
agaacgtgga ctccaacgtc aaagggcgaa aaaccgtcta tcagggcgat ggcccactac   6780
gtgaaccatc accctaatca agttttttgg ggtcgaggtg ccgtaaagca ctaaatcgga   6840
accctaaagg gagcccccga tttagagctt gacggggaaa gccggcgaac gtggcgagaa   6900
aggaagggaa gaaagcgaaa ggagcgggcg ctagggcgct ggcaagtgta gcggtcacgc   6960
tgcgcgtaac caccacaccc gccgcgctta atgcgccgct acagggcgcg tcaggtggca   7020
cttttcgggg aaatgtgcgc ggaaccccta tttgtttatt tttctaaata cattcaaata   7080
tgtatccgct catgagacaa taaccctgat aaatgcttca ataatattga aaaaggaaga   7140
gtcctgaggc ggaaagaacc agctgtggaa tgtgtgtcag ttagggtgtg gaaagtcccc   7200
aggctcccca gcaggcagaa gtatgcaaag catgcatctc aattagtcag caaccaggtg   7260
tggaaagtcc ccaggctccc cagcaggcag aagtatgcaa agcatgcatc tcaattagtc   7320
agcaaccata gtcccgcccc taactccgcc catcccgccc ctaactccgc ccagttccgc   7380
ccattctccg ccccatggct gactaatttt ttttatttat gcagaggccg aggccgcctc   7440
ggcctctgag ctattccaga agtagtgagg aggctttttt ggaggcctag gcttttgcaa   7500
agatcgatca agagacagga tgaggatcgt ttcgcatgat tgaacaagat ggattgcacg   7560
caggttctcc ggccgcttgg gtggagaggc tattcggcta tgactgggca caacagacaa   7620
tcggctgctc tgatgccgcc gtgttccggc tgtcagcgca ggggcgcccg gttctttttg   7680
tcaagaccga cctgtccggt gccctgaatg aactgcaaga cgaggcagcg cggctatcgt   7740
```

```
ggctggccac gacgggcgtt ccttgcgcag ctgtgctcga cgttgtcact gaagcgggaa   7800

gggactggct gctattgggc gaagtgccgg ggcaggatct cctgtcatct caccttgctc   7860

ctgccgagaa agtatccatc atggctgatg caatgcggcg gctgcatacg cttgatccgg   7920

ctacctgccc attcgaccac caagcgaaac atcgcatcga gcgagcacgt actcggatgg   7980

aagccggtct tgtcgatcag gatgatctgg acgaagagca tcaggggctc gcgccagccg   8040

aactgttcgc caggctcaag gcgagcatgc ccgacggcga ggatctcgtc gtgacccatg   8100

gcgatgcctg cttgccgaat atcatggtgg aaaatggccg cttttctgga ttcatcgact   8160

gtggccggct gggtgtggcg gaccgctatc aggacatagc gttggctacc cgtgatattg   8220

ctgaagagct tggcggcgaa tgggctgacc gcttcctcgt gctttacggt atcgccgctc   8280

ccgattcgca gcgcatcgcc ttctatcgcc ttcttgacga gttcttctga gcgggactct   8340

ggggttcgaa atgaccgacc aagcgacgcc caacctgcca tcacgagatt tcgattccac   8400

cgccgccttc tatgaaaggt tgggcttcgg aatcgttttc cgggacgccg gctggatgat   8460

cctccagcgc ggggatctca tgctggagtt cttcgcccac cctaggggga ggctaactga   8520

aacacggaag gagacaatac cggaaggaac ccgcgctatg acggcaataa aaagacagaa   8580

taaaacgcac ggtgttgggt cgtttgttca taaacgcggg gttcggtccc agggctggca   8640

ctctgtcgat accccaccga gaccccattg gggccaatac gcccgcgttt cttccttttc   8700

cccaccccac cccccaagtt cgggtgaagg cccagggctc gcagccaacg tcggggcggc   8760

aggccctgcc atagcctcag gttactcata tatactttag attgatttaa aacttcattt   8820

ttaatttaaa aggatctagg tgaagatcct ttttgataat ctcatgacca aaatccctta   8880

acgtgagttt tcgttccact gagcgtcaga ccccgtagaa aagatcaaag gatcttcttg   8940

agatcctttt tttctgcgcg taatctgctg cttgcaaaca aaaaaaccac cgctaccagc   9000

ggtggtttgt ttgccggatc aagagctacc aactcttttt ccgaaggtaa ctggcttcag   9060

cagagcgcag ataccaaata ctgtccttct agtgtagccg tagttaggcc accacttcaa   9120

gaactctgta gcaccgccta catacctcgc tctgctaatc ctgttaccag tggctgctgc   9180

cagtggcgat aagtcgtgtc ttaccgggtt ggactcaaga cgatagttac cggataaggc   9240

gcagcggtcg ggctgaacgg ggggttcgtg cacacagccc agcttggagc gaacgaccta   9300

caccgaactg agatacctac agcgtgagct atgagaaagc gccacgcttc ccgaagggag   9360

aaaggcggac aggtatccgg taagcggcag ggtcggaaca ggagagcgca cgagggagct   9420

tccaggggga aacgcctggt atctttatag tcctgtcggg tttcgccacc tctgacttga   9480

gcgtcgattt ttgtgatgct cgtcaggggg gcggagccta tggaaaaacg ccagcaacgc   9540

ggccttttta cggttcctgg ccttttgctg gccttttgct cacatgttct ttcctgcgtt   9600

atcccctgat tctgtggata accgtattac cgccatgcat                         9640
```

<210> SEQ ID NO 5
<211> LENGTH: 9343
<212> TYPE: DNA
<213> ORGANISM: Artificial Sequence
<220> FEATURE:
<223> OTHER INFORMATION: Sequence of expression vector pHgra8-EYFP-NA-A3'

<400> SEQUENCE: 5

```
agatctaacc agcaaaggta gcaacagtag aggttagcaa tgttaccttt gtcaccgtca     60

gtgacaggca caagaacgaa cttgttacac tcgagataca tagcttctgt aaaactgaat    120
```

-continued

```
cattcgcggt ttctgtttgc tctgctgaca tctattggtc cattgttgga gactctgttg    180
ctttttctgt tttttaaatt cttatagaac ccgctattgc tgtcgtggtg agccatccgc    240
cgcgaaacgg ctgatgctcg actcattgtg gctgctttgc ccattcgctg cggttagttg    300
cagaaaaaaa cagcggcaca aatagctgct cccccaggtg ataaatatctc tacaacagca   360
ttctaggatg tgcttgaatg tcccgccctc ttcctttcca aatagttgct cgcgcagttg    420
atgatatcgt aacagcagcg ttctagtgag tatttgaata cccagccctg ttgttttcaa    480
agccacgcaa cagcagcagt tacagaagca tataaagccc atgcagctga tgctgctgca    540
gctgaactct ctactgggaa aagcatgcat catgcaaaat gctgtgcaac ctgcggggca    600
aagcatgcaa aaagctcccc tctaagggga tgtgtgtgac tctcaatagg cgtactggtt    660
ttgctgccag aagcttccgc tagtgtgacc aatacattta gagtttgcca ttaccactgg    720
tgttaaggac ctccgtaaag agcttttgga aggcggcagt tcgagcaagc aggagctgga    780
ctgcctttaa cagccattgg caagtgaaac catcgaatca ctgttactca cacagacggg    840
catttgctcg cactttttttg gttagggcct caagggaatt tggggcagca gtggattagc   900
acctccactg ctcttttcgc caattcttcc gtcaccccgg gtttacaaac gaacgagctc    960
gtagctgtag tccccggcgt ttgtactgtg ccccgcagta agtgggacgc actaaggtcc    1020
tcctacttta acagttcgag ttccttcttc tcgcgctcgg ctttccgctc tcgcatgtat    1080
cttgcaccac tgcaactgca acattcagtg acttagccgt cagatggcat ctgcagtgct    1140
gttgtcatta ataaatttca tcgttgctgt acatagcctg tttatcacgc gactatattg    1200
ctaaacgatg caaagacaga agtgccagca gcagcagaag cagcctaaac ggcgcaaacc    1260
ctgtcgggtg gcagcccgtt aatttcgaag catagtcatg cgtgcttgca gcacttcaga    1320
cactcaaaaa aataatgcat atctccacac aaatgcaggc atattctcaa cgtctcagta    1380
ggttgctatg acctgaactg tggggggtgg ttgttataca gaaggcgacg taaacgaagt    1440
cctgcgggga ctgaacaata atctacggat gtatttagtc ctaaaagcac aaacttgatg    1500
gcagttggca gaagaaacat ttaaagaatt agttttaacc aaaaggctac gagcgaggga    1560
ggaggcgcgg ggatgctgca gcacctcctc taccaccctg tgtacttccg tacgttgcac    1620
aggtggcggt gaataacgtc cgtcggttct acttgcatcc ttaagctgtt attaaagcgt    1680
aattttgcaa aaaattagga tagagaataa aatatttgga aaacaatggc gctttatttg    1740
ctgaaacaac aagcgaggct gggggtcggc tgttcgcccg ggcgcgggct agcaggctag    1800
ctgcgcagag actgcatgtt cccccactgt acgtgcaggg tgcgcgtgtt gttgttcgtg    1860
atggtatcgg cgcgcgtatg tctcacatcc gttatttaga ggctacaacg agactgtctg    1920
ttgtgtctgt tccatagaaa accaaaatgg ctttaccatt gcgtgtttcg gccacggtgt    1980
tcgtggtctt cgctgtcttt ggtgtagctc gcgccggtac cgtcgccacc atggtgagca    2040
agggcgagga gctgttcacc ggggtggtgc ccatcctggt cgagctggac ggcgacgtaa    2100
acggccacaa gttcagcgtg tccggcgagg gcgagggcga tgccacctac ggcaagctga    2160
ccctgaagtt catctgcacc accggcaagc tgcccgtgcc ctggcccacc ctcgtgacca    2220
ccttcggcta cggcctgcag tgcttcgccc gctaccccga ccacatgaag cagcacgact    2280
tcttcaagtc cgccatgccc gaaggctacg tccaggagcg caccatcttc ttcaaggacg    2340
acggcaacta caagacccgc gccgaggtga agttcgaggg cgacaccctg gtgaaccgca    2400
tcgagctgaa gggcatcgac ttcaaggagg acggcaacat cctggggcac aagctggagt    2460
acaactacaa cagccacaac gtctatatca tggccgacaa gcagaagaac ggcatcaagg    2520
```

-continued

```
tgaacttcaa gatccgccac aacatcgagg acggcagcgt gcagctcgcc gaccactacc   2580
agcagaacac ccccatcggc gacggccccg tgctgctgcc cgacaaccac tacctgagct   2640
accagtccgc cctgagcaaa gaccccaacg agaagcgcga tcacatggtc ctgctggagt   2700
tcgtgaccgc cgccgggatc actctcggca tggacgagct gtacaagaag cttagccaac   2760
cggtcgccac catgaatcca aatcagaaga taataaccat tggatcaatc tgtatgataa   2820
ttggaatagt tagcttgatg ttacaaattg ggaacataat ctcaatatgg gttagtcatt   2880
caattcagac agggaatcaa caccaagctg aaccatgcaa tcaaagcatt attacttatg   2940
aaaacaacac ctgggtaaat cagacatatg tcaacatcag caataccaat tttcttactg   3000
agaaagctgt ggcttcagta acattagcgg gcaattcatc tctttgccct attagtggat   3060
gggctgtata cagtaaagac aacggtataa gaatcggttc caaggggggat gtgtttgtta   3120
taagagagcc gttcatctca tgctcccact tggaatgcag aactttcttt ttgactcagg   3180
gagccttgct gaatgacaag cattctaatg ggaccgtcaa agacagaagc ccttacagaa   3240
cattgatgag ttgtcctgtg ggtgaggctc cttccccata taactcgagg tttgagtctg   3300
ttgcttggtc ggcaagtgct tgtcatgatg gcactagttg gttgacaatt ggaatttctg   3360
gcccagacaa tggggctgtg gctgtattga aatacaatgg cataataaca gacacaatca   3420
agagttggag gaacaacata ctgagaactc aagagtctga atgtgcatgt gtaaatggct   3480
cttgctttac tgtaatgact gatggaccaa gtaatgggca ggcttcatat aagatcttca   3540
aaatagaaaa agggaaagta gttaaatcag tcgaattgaa tgcccctaat tatcactatg   3600
aggagtgctc ctgttatcct gatgctggcg aaatcacatg tgtgtgcagg gataactggc   3660
atggctcaaa tcggccatgg gtatctttca atcaaaattt ggagtatcaa ataggatata   3720
tatgcagtgg agttttcgga gacaatccac gccccaatga tgggacaggc agttgtggtc   3780
cggtgtcccc taacggggca tatggaataa aagggttttc atttaaatac ggcaatggtg   3840
tttggatcgg gagaaccaaa agcactaatt ccaggagcgg ctttgaaatg atttgggatc   3900
caaatgggtg gactggaacg gacagtaatt tttcggtgaa gcaagatatc gtagctataa   3960
ctgattggtc aggatatagc gggagttttg tccagcatcc agaactgaca ggattagatt   4020
gcataagacc ttgtttctgg gttgagctaa tcagagggcg gcccaaagag agcacaattt   4080
ggactagtgg gagcagcata tccttttgtg gtgtaaatag tgacactgtg ggttggtctt   4140
ggccagacgg tgctgagttg ccattcacca ttgacaagta ggcggccgcg ggaattcgat   4200
tggccgcgtt tgcagcagag tagttcatga cttgcgaaac ggcctctcga ttaataatac   4260
gctttgccgc aacgtgaagt aggcgttatt gtgtgctgcc tgtcgctgag ctcctgcatc   4320
gagcggcaag ggttcaaccc gagcgcaaat tctgtggaaa tagctggaca aaagcatctg   4380
cgacgggtgg gggcaggcgc agctagctgt tgctcccgac atcagtcatg gaaatgcgtt   4440
tcaggctaag caagtagctg cccgcctggt gggaagatga ggctaggaac tgctatgttt   4500
gcccctcact tggcggtatt gcagtgtagt acgtgcattg tgaacccaga gaaatgtgct   4560
ccgcgtgacg cagcgaggca caggggaaca gcaagagggg ccgttattgc tcagcgtgct   4620
ggaccccctt gttccttcaa accttactta tgagggctta cgcatcgcac ctgatgggtc   4680
ggtgtagcgt gatcatttca ctgttcagta gtaggtatgg gaggagtgta gttggcagga   4740
tgtaggagct ttgcaagcgg tggaacggtt gagatgagta gtgaacagag gctttgccca   4800
atgtcggata gtgagtgttt ctcgagcacg aaacgtgcaa ggcaacaggt tactgtaggt   4860
ttatgtagtt ggcaagagtg ggccttgccc agtattcggt agtaagtgtc aagcacgaca   4920
```

```
ccagattgcg aagcaacagg taattgtagg tttacgtatc gtacgttttt catgggagtg   4980

tgacggaaag ttgtgggtag cagggtccgg gggagtctgc ggcaagcagt tcaacagatt   5040

gatggaacag aaagattaag aggcggagtg tccgctgttg ctgtgggcag aaagagggcg   5100

gcgtagagag gcatttagtg gatgcttttg aggagttctg ggaggtcatc agtagtgggg   5160

aaggtctacc gcaccgtctg gtcggcctat tagttaatgc ccacatgagg cgatcttttg   5220

gtggtgcgtg acggggtcag tcattggatt tggtatctgc cgctccattt gtagctagga   5280

gagcctctga tgccgtgaca tcttgctagg ttcgcactgt ttccacaacg actactttgt   5340

ttggtcattt tcaccgtgaa agtatgttca ccttggagag agaaaatttg agagagctct   5400

gagttgttgg aacagcccaa gtagctgact ctcataggat actactaaag ccaaacggcg   5460

cgttgtagcg ctcatctgca gggattgatc tttaaaaaaa tgatctttta aggttcatgc   5520

catacttatt gagttcgcta ggtgtcaact tgtcgaacac attcttgagg tgttgcgtat   5580

ctgggcgctc ccaggggttc catgtgaagc aattgtccag cgttgcgcgg acgctcggat   5640

gaaaccaggc aggaacggta ggtttgcgac gattgtacaa gagcgcgtgt attactccta   5700

cgcatccaca gaaatcagca ttggtaatcg tcgtggctgt tgcaaggtct ggtagcaaag   5760

ctgcatatat ttgcttgact gaatttcact taccctcgtt agagtgtatg tcttcgtagg   5820

gtatcggacc ccccagtatt tcaattaggc agcatgcaag cccccaaata tcaagcttct   5880

catccacgta gttgccttcc acgaagcatt caggagccat gtagcgggga gaccctccgt   5940

tgtcctccaa tttaagcttt ccgtgctgct ctaatgaccg tgtcttgcca aagtcgcaga   6000

gccgaatgtt gtactgcaca cataagttga acatcacaga gaaaccaagg gagaaattca   6060

ctcacagggc tgtgcccacc ctcattcatc ctggtagaat agccaaccaa ttgcacccac   6120

gtgaagccaa aacgagcgaa cattcatgac agcaagttat gaattttggc gacctgtgtt   6180

ggtaaaaatg aaaaggaggc tacgaagaat ttgagcgttt ggtgcgaatc ctgcttacat   6240

ctcggtcgct taaggcgtaa attgtaagcg ttaatatttt gttaaaattc gcgttaaatt   6300

tttgttaaat cagctcattt tttaaccaat aggccgaaat cggcaaaatc ccttataaat   6360

caaaagaata gaccgagata gggttgagtg ttgttccagt ttggaacaag agtccactat   6420

taaagaacgt ggactccaac gtcaaagggc gaaaaaccgt ctatcagggc gatggcccac   6480

tacgtgaacc atcaccctaa tcaagttttt tggggtcgag gtgccgtaaa gcactaaatc   6540

ggaaccctaa agggagcccc cgatttagag cttgacgggg aaagccggcg aacgtggcga   6600

gaaaggaagg gaagaaagcg aaaggagcgg gcgctagggc gctggcaagt gtagcggtca   6660

cgctgcgcgt aaccaccaca cccgccgcgc ttaatgcgcc gctacagggc gcgtcaggtg   6720

gcacttttcg gggaaatgtg cgcggaaccc ctatttgttt atttttctaa atacattcaa   6780

atatgtatcc gctcatgaga caataaccct gataaatgct tcaataatat tgaaaaagga   6840

agagtcctga ggcggaaaga accagctgtg gaatgtgtgt cagttagggt gtggaaagtc   6900

cccaggctcc ccagcaggca gaagtatgca aagcatgcat ctcaattagt cagcaaccag   6960

gtgtggaaag tccccaggct ccccagcagg cagaagtatg caaagcatgc atctcaatta   7020

gtcagcaacc atagtcccgc ccctaactcc gcccatcccg cccctaactc cgcccagttc   7080

cgcccattct ccgccccatg gctgactaat tttttttatt tatgcagagg ccgaggccgc   7140

ctcggcctct gagctattcc agaagtagtg aggaggcttt tttggaggcc taggcttttg   7200

caaagatcga tcaagagaca ggatgaggat cgtttcgcat gattgaacaa gatggattgc   7260

acgcaggttc tccggccgct tgggtggaga ggctattcgg ctatgactgg gcacaacaga   7320
```

```
caatcggctg ctctgatgcc gccgtgttcc ggctgtcagc gcaggggcgc ccggttcttt   7380

ttgtcaagac cgacctgtcc ggtgccctga atgaactgca agacgaggca gcgcggctat   7440

cgtggctggc cacgacgggc gttccttgcg cagctgtgct cgacgttgtc actgaagcgg   7500

gaagggactg gctgctattg ggcgaagtgc cggggcagga tctcctgtca tctcaccttg   7560

ctcctgccga gaaagtatcc atcatggctg atgcaatgcg gcggctgcat acgcttgatc   7620

cggctacctg cccattcgac caccaagcga aacatcgcat cgagcgagca cgtactcgga   7680

tggaagccgg tcttgtcgat caggatgatc tggacgaaga gcatcagggg ctcgcgccag   7740

ccgaactgtt cgccaggctc aaggcgagca tgcccgacgg cgaggatctc gtcgtgaccc   7800

atggcgatgc ctgcttgccg aatatcatgg tggaaaatgg ccgcttttct ggattcatcg   7860

actgtggccg gctgggtgtg gcggaccgct atcaggacat agcgttggct acccgtgata   7920

ttgctgaaga gcttggcggc gaatgggctg accgcttcct cgtgctttac ggtatcgccg   7980

ctcccgattc gcagcgcatc gccttctatc gccttcttga cgagttcttc tgagcgggac   8040

tctggggttc gaaatgaccg accaagcgac gcccaacctg ccatcacgag atttcgattc   8100

caccgccgcc ttctatgaaa ggttgggctt cggaatcgtt ttccgggacg ccggctggat   8160

gatcctccag cgcggggatc tcatgctgga gttcttcgcc caccctaggg ggaggctaac   8220

tgaaacacgg aaggagacaa taccggaagg aacccgcgct atgacggcaa taaaaagaca   8280

gaataaaacg cacggtgttg ggtcgtttgt tcataaacgc ggggttcggt cccagggctg   8340

gcactctgtc gataccccac cgagacccca ttggggccaa tacgcccgcg tttcttcctt   8400

ttccccaccc caccccccaa gttcgggtga aggcccaggg ctcgcagcca acgtcggggc   8460

ggcaggccct gccatagcct caggttactc atatatactt tagattgatt taaaacttca   8520

tttttaattt aaaaggatct aggtgaagat cctttttgat aatctcatga ccaaaatccc   8580

ttaacgtgag ttttcgttcc actgagcgtc agaccccgta gaaaagatca aaggatcttc   8640

ttgagatcct ttttttctgc gcgtaatctg ctgcttgcaa acaaaaaaac caccgctacc   8700

agcggtggtt tgtttgccgg atcaagagct accaactctt tttccgaagg taactggctt   8760

cagcagagcg cagataccaa atactgtcct tctagtgtag ccgtagttag gccaccactt   8820

caagaactct gtagcaccgc ctacatacct cgctctgcta atcctgttac cagtggctgc   8880

tgccagtggc gataagtcgt gtcttaccgg gttggactca agacgatagt taccggataa   8940

ggcgcagcgg tcgggctgaa cggggggttc gtgcacacag cccagcttgg agcgaacgac   9000

ctacaccgaa ctgagatacc tacagcgtga gctatgagaa agcgccacgc ttcccgaagg   9060

gagaaaggcg gacaggtatc cggtaagcgg cagggtcgga acaggagagc gcacgaggga   9120

gcttccaggg ggaaacgcct ggtatcttta tagtcctgtc gggtttcgcc acctctgact   9180

tgagcgtcga tttttgtgat gctcgtcagg ggggcggagc ctatggaaaa acgccagcaa   9240

cgcggccttt ttacggttcc tggccttttg ctggcctttt gctcacatgt tctttcctgc   9300

gttatcccct gattctgtgg ataaccgtat taccgccatg cat                     9343
```

```
<210> SEQ ID NO 6
<211> LENGTH: 9430
<212> TYPE: DNA
<213> ORGANISM: Artificial Sequence
<220> FEATURE:
<223> OTHER INFORMATION: Sequence of expression vector
      pHgra8-EYFP-NP-A3'

<400> SEQUENCE: 6

agatctaacc agcaaaggta gcaacagtag aggttagcaa tgttaccttt gtcaccgtca     60
```

```
gtgacaggca caagaacgaa cttgttacac tcgagataca tagcttctgt aaaactgaat    120
cattcgcggt ttctgtttgc tctgctgaca tctattggtc cattgttgga gactctgttg    180
ctttttctgt tttttaaatt cttatagaac ccgctattgc tgtcgtggtg agccatccgc    240
cgcgaaacgg ctgatgctcg actcattgtg gctgctttgc ccattcgctg cggttagttg    300
cagaaaaaaa cagcggcaca aatagctgct cccccaggtg ataatatctc tacaacagca    360
ttctaggatg tgcttgaatg tcccgccctc ttcctttcca aatagttgct cgcgcagttg    420
atgatatcgt aacagcagcg ttctagtgag tatttgaata cccagccctg ttgttttcaa    480
agccacgcaa cagcagcagt tacagaagca tataaagccc atgcagctga tgctgctgca    540
gctgaactct ctactgggaa aagcatgcat catgcaaaat gctgtgcaac ctgcggggca    600
aagcatgcaa aaagctcccc tctaagggga tgtgtgtgac tctcaatagg cgtactggtt    660
ttgctgccag aagcttccgc tagtgtgacc aatacattta gagtttgcca ttaccactgg    720
tgttaaggac ctccgtaaag agcttttgga aggcggcagt tcgagcaagc aggagctgga    780
ctgcctttaa cagccattgg caagtgaaac catcgaatca ctgttactca cacagacggg    840
catttgctcg cacttttttg gttagggcct caagggaatt tggggcagca gtggattagc    900
acctccactg ctcttttcgc caattcttcc gtcaccccgg gtttacaaac gaacgagctc    960
gtagctgtag tccccggcgt ttgtactgtg ccccgcagta agtgggacgc actaaggtcc   1020
tcctacttta acagttcgag ttccttcttc tcgcgctcgg ctttccgctc tcgcatgtat   1080
cttgcaccac tgcaactgca acattcagtg acttagccgt cagatggcat ctgcagtgct   1140
gttgtcatta ataaatttca tcgttgctgt acatagcctg tttatcacgc gactatattg   1200
ctaaacgatg caaagacaga agtgccagca gcagcagaag cagcctaaac ggcgcaaacc   1260
ctgtcgggtg gcagcccgtt aatttcgaag catagtcatg cgtgcttgca gcacttcaga   1320
cactcaaaaa aataatgcat atctccacac aaatgcaggc atattctcaa cgtctcagta   1380
ggttgctatg acctgaactg tggggggtgg ttgttataca gaaggcgacg taaacgaagt   1440
cctgcgggga ctgaacaata atctacggat gtatttagtc ctaaaagcac aaacttgatg   1500
gcagttggca gaagaaacat ttaaagaatt agttttaacc aaaaggctac gagcgaggga   1560
ggaggcgcgg ggatgctgca gcacctcctc taccaccctg tgtacttccg tacgttgcac   1620
aggtggcggt gaataacgtc cgtcggttct acttgcatcc ttaagctgtt attaaagcgt   1680
aattttgcaa aaaattagga tagagaataa aatatttgga aaacaatggc gctttatttg   1740
ctgaaacaac aagcgaggct gggggtcggc tgttcgcccg ggcgcgggct agcaggctag   1800
ctgcgcagag actgcatgtt cccccactgt acgtgcaggg tgcgcgtgtt gttgttcgtg   1860
atggtatcgg cgcgcgtatg tctcacatcc gttatttaga ggctacaacg agactgtctg   1920
ttgtgtctgt tccatagaaa accaaaatgg ctttaccatt gcgtgtttcg gccacggtgt   1980
tcgtggtctt cgctgtcttt ggtgtagctc gcgccggtac cgtcgccacc atggtgagca   2040
agggcgagga gctgttcacc ggggtggtgc ccatcctggt cgagctggac ggcgacgtaa   2100
acggccacaa gttcagcgtg tccggcgagg gcgagggcga tgccacctac ggcaagctga   2160
ccctgaagtt catctgcacc accggcaagc tgcccgtgcc ctggcccacc ctcgtgacca   2220
ccttcggcta cggcctgcag tgcttcgccc gctaccccga ccacatgaag cagcacgact   2280
tcttcaagtc cgccatgccc gaaggctacg tccaggagcg caccatcttc ttcaaggacg   2340
acggcaacta caagacccgc gccgaggtga agttcgaggg cgacaccctg gtgaaccgca   2400
tcgagctgaa gggcatcgac ttcaaggagg acggcaacat cctggggcac aagctggagt   2460
```

-continued

```
acaactacaa cagccacaac gtctatatca tggccgacaa gcagaagaac ggcatcaagg   2520
tgaacttcaa gatccgccac aacatcgagg acggcagcgt gcagctcgcc gaccactacc   2580
agcagaacac ccccatcggc gacggccccg tgctgctgcc cgacaaccac tacctgagct   2640
accagtccgc cctgagcaaa gaccccaacg agaagcgcga tcacatggtc ctgctggagt   2700
tcgtgaccgc cgccgggatc actctcggca tggacgagct gtacaagaag cttagccaac   2760
cggtcgccac catggcgtct caaggcacca aacgatctta tgaacagatg gaaactggtg   2820
gagaacgcca gaatgctact gagatcagag catctgttgg aagaatggtc ggtggaattg   2880
ggaggtttta tatacagatg tgcactgaac tcaaactcag tgactatgaa gggaggctga   2940
ttcagaacag cataacaata gagagaatgg ttctctctgc atttgatgaa aggaggaaca   3000
aatacctgga agaacatccc agtgcgggga aagacccaaa gaaaactgga ggtccaatct   3060
accgaaggag agacgggaag tgggtgagag agctgattct gtatgataaa gaggagatca   3120
ggaggatttg gcgccaagcg aacaatggag aagatgcaac tgctggtctc actcatctga   3180
tgatctggca ttccaatcta aatgatgcca cataccagag gacaagagct ctcgtgcgta   3240
ctgggatgga ccccagaatg tgttctctaa tgcaaggatc aactctcccg aggagatctg   3300
gagctgcagg tgcagcagta aagggagtcg gaacgatggt gatggaacta attcggatga   3360
taaagcgagg gattaatgat cggaatttct ggagaggtga aaatgggcga agaacgagga   3420
ttgcatatga gagaatgtgc aacatcctca aagggaaatt ccaaacagca gcacaaagag   3480
caatgatgga ccaggtacgg gaaagcagga atcctgggaa tgccgaaatt gaagatctca   3540
tcttcctggc acggtctgca ctcatcctga gaggatcagt ggctcacaag tcctgcttgc   3600
ctgcttgtgt gtacgggctt gctgtagcca gtggatatga ctttgagaga gaagggtatt   3660
ctctggtcgg gattgatccc tttcgtctgc tgcaaaacag ccaagtcttc agtctaatta   3720
gaccaaatga gaacccagca cataaaagtc aactggtatg gatggcatgc cattctgcag   3780
catttgaaga tctgagggtc tcaagtttca tcagagggac aagagtagtt ccaaggggac   3840
aactatctac tagaggagtt caaattgctt caaatgagaa catggataca atggactcca   3900
acactctaga actgagaagc agatattggg ctataagaac caggagtgga ggaaacacca   3960
atcagcagag agcatctgca ggacaaatca gtgtacagcc tactttttcg gtacagagaa   4020
atcttccctt cgaaagagcg accattatgg cggcatttac agggaataca gagggcagaa   4080
catctgacat gaggactgaa ataataagaa taatggaaag cgcccgacca gaagatgtgt   4140
ctttccaggg gcggggagtc ttcgagctct cggacgaaaa ggcaacgaac ccgatcgtgc   4200
cttcctttga catgagtaat gaaggatctt acttcttcgg agacaatgca gaggagtttg   4260
agaattaagc ggccgcggga attcgattgg ccgcgtttgc agcagagtag ttcatgactt   4320
gcgaaacggc ctctcgatta ataatacgct ttgccgcaac gtgaagtagg cgttattgtg   4380
tgctgcctgt cgctgagctc ctgcatcgag cggcaagggg ttcaaccgag cgcaaattct   4440
gtggaaatag ctggacaaaa gcatctgcga cgggtggggg caggcgcagc tagctgttgc   4500
tcccgacatc agtcatggaa atgcgtttca ggctaagcaa gtagctgccc gcctggtggg   4560
aagatgaggc taggaactgc tatgtttgcc cctcacttgg cggtattgca gtgtagtacg   4620
tgcattgtga acccagagaa atgtgctccg cgtgacgcag cgaggcacag gggaacagca   4680
agaggggccg ttattgctca gcgtgctgga ccccccttgtt ccttcaaacc ttacttatga   4740
gggcttacgc atcgcacctg atgggtcggt gtagcgtgat catttcactg ttcagtagta   4800
ggtatgggag gagtgtagtt ggcaggatgt aggagctttg caagcggtgg aacggttgag   4860
```

```
atgagtagtg aacagaggct ttgcccaatg tcggatagtg agtgtttctc gagcacgaaa   4920
cgtgcaaggc aacaggttac tgtaggttta tgtagttggc aagagtgggc cttgcccagt   4980
attcggtagt aagtgtcaag cacgacacca gattgcgaag caacaggtaa ttgtaggttt   5040
acgtatcgta cgtttttcat gggagtgtga cggaaagttg tgggtagcag ggtccggggg   5100
agtctgcggc aagcagttca acagattgat ggaacagaaa gattaagagg cggagtgtcc   5160
gctgttgctg tgggcagaaa gagggcggcg tagagaggca tttagtggat gcttttgagg   5220
agttctggga ggtcatcagt agtggggaag gtctaccgca ccgtctggtc ggcctattag   5280
ttaatgccca catgaggcga tcttttggtg gtgcgtgacg gggtcagtca ttggatttgg   5340
tatctgccgc tccatttgta gctaggagag cctctgatgc cgtgacatct tgctaggttc   5400
gcactgtttc cacaacgact actttgtttg gtcattttca ccgtgaaagt atgttcacct   5460
tggagagaga aaatttgaga gagctctgag ttgttggaac agcccaagta gctgactctc   5520
ataggatact actaaagcca aacggcgcgt tgtagcgctc atctgcaggg attgatcttt   5580
aaaaaaatga tcttttaagg ttcatgccat acttattgag ttcgctaggt gtcaacttgt   5640
cgaacacatt cttgaggtgt tgcgtatctg ggcgctccca ggggttccat gtgaagcaat   5700
tgtccagcgt tgcgcggacg ctcggatgaa accaggcagg aacggtaggt ttgcgacgat   5760
tgtacaagag cgcgtgtatt actcctacgc atccacagaa atcagcattg gtaatcgtcg   5820
tggctgttgc aaggtctggt agcaaagctg catatatttg cttgactgaa tttcacttac   5880
cctcgttaga gtgtatgtct tcgtagggta tcggaccccc cagtatttca attaggcagc   5940
atgcaagccc ccaaatatca agcttctcat ccacgtagtt gccttccacg aagcattcag   6000
gagccatgta gcggggagac cctccgttgt cctccaattt aagctttccg tgctgctcta   6060
atgaccgtgt cttgccaaag tcgcagagcc gaatgttgta ctgcacacat aagttgaaca   6120
tcacagagaa accaagggag aaattcactc acagggctgt gcccaccctc attcatcctg   6180
gtagaatagc caaccaattg cacccacgtg aagccaaaac gagcgaacat tcatgacagc   6240
aagttatgaa ttttggcgac ctgtgttggt aaaaatgaaa aggaggctac gaagaatttg   6300
agcgtttggt gcgaatcctg cttacatctc ggtcgcttaa ggcgtaaatt gtaagcgtta   6360
atattttgtt aaaattcgcg ttaaattttt gttaaatcag ctcatttttt aaccaatagg   6420
ccgaaatcgg caaaatccct tataaatcaa aagaatagac cgagataggg ttgagtgttg   6480
ttccagtttg gaacaagagt ccactattaa agaacgtgga ctccaacgtc aaagggcgaa   6540
aaaccgtcta tcagggcgat ggcccactac gtgaaccatc accctaatca agttttttgg   6600
ggtcgaggtg ccgtaaagca ctaaatcgga accctaaagg gagcccccga tttagagctt   6660
gacggggaaa gccggcgaac gtggcgagaa aggaagggaa gaaagcgaaa ggagcgggcg   6720
ctagggcgct ggcaagtgta gcggtcacgc tgcgcgtaac caccacaccc gccgcgctta   6780
atgcgccgct acagggcgcg tcaggtggca cttttcgggg aaatgtgcgc ggaaccccta   6840
tttgtttatt tttctaaata cattcaaata tgtatccgct catgagacaa taaccctgat   6900
aaatgcttca ataatattga aaaaggaaga gtcctgaggc ggaaagaacc agctgtggaa   6960
tgtgtgtcag ttagggtgtg gaaagtcccc aggctcccca gcaggcagaa gtatgcaaag   7020
catgcatctc aattagtcag caaccaggtg tggaaagtcc ccaggctccc cagcaggcag   7080
aagtatgcaa agcatgcatc tcaattagtc agcaaccata gtcccgcccc taactccgcc   7140
catcccgccc ctaactccgc ccagttccgc ccattctccg ccccatggct gactaatttt   7200
ttttatttat gcagaggccg aggccgcctc ggcctctgag ctattccaga agtagtgagg   7260
```

```
aggcttttt ggaggcctag gcttttgcaa agatcgatca agagacagga tgaggatcgt   7320
ttcgcatgat tgaacaagat ggattgcacg caggttctcc ggccgcttgg gtggagaggc   7380
tattcggcta tgactgggca caacagacaa tcggctgctc tgatgccgcc gtgttccggc   7440
tgtcagcgca ggggcgcccg gttctttttg tcaagaccga cctgtccggt gccctgaatg   7500
aactgcaaga cgaggcagcg cggctatcgt ggctggccac gacgggcgtt ccttgcgcag   7560
ctgtgctcga cgttgtcact gaagcgggaa gggactggct gctattgggc gaagtgccgg   7620
ggcaggatct cctgtcatct caccttgctc ctgccgagaa agtatccatc atggctgatg   7680
caatgcggcg gctgcatacg cttgatccgg ctacctgccc attcgaccac caagcgaaac   7740
atcgcatcga gcgagcacgt actcggatgg aagccggtct tgtcgatcag gatgatctgg   7800
acgaagagca tcaggggctc gcgccagccg aactgttcgc caggctcaag gcgagcatgc   7860
ccgacggcga ggatctcgtc gtgacccatg gcgatgcctg cttgccgaat atcatggtgg   7920
aaaatggccg cttttctgga ttcatcgact gtggccggct gggtgtggcg gaccgctatc   7980
aggacatagc gttggctacc cgtgatattg ctgaagagct tggcggcgaa tgggctgacc   8040
gcttcctcgt gctttacggt atcgccgctc ccgattcgca gcgcatcgcc ttctatcgcc   8100
ttcttgacga gttcttctga gcgggactct ggggttcgaa atgaccgacc aagcgacgcc   8160
caacctgcca tcacgagatt tcgattccac cgccgccttc tatgaaaggt tgggcttcgg   8220
aatcgttttc cgggacgccg gctggatgat cctccagcgc ggggatctca tgctggagtt   8280
cttcgcccac cctaggggga ggctaactga aacacggaag gagacaatac cggaaggaac   8340
ccgcgctatg acggcaataa aaagacagaa taaaacgcac ggtgttgggt cgtttgttca   8400
taaacgcggg gttcggtccc agggctggca ctctgtcgat accccaccga gaccccattg   8460
gggccaatac gcccgcgttt cttccttttc cccaccccac cccccaagtt cgggtgaagg   8520
cccagggctc gcagccaacg tcggggcggc aggccctgcc atagcctcag gttactcata   8580
tatactttag attgatttaa aacttcattt ttaatttaaa aggatctagg tgaagatcct   8640
ttttgataat ctcatgacca aaatccctta acgtgagttt tcgttccact gagcgtcaga   8700
ccccgtagaa aagatcaaag gatcttcttg agatcctttt tttctgcgcg taatctgctg   8760
cttgcaaaca aaaaaaccac cgctaccagc ggtggtttgt ttgccggatc aagagctacc   8820
aactcttttt ccgaaggtaa ctggcttcag cagagcgcag ataccaaata ctgtccttct   8880
agtgtagccg tagttaggcc accacttcaa gaactctgta gcaccgccta catacctcgc   8940
tctgctaatc ctgttaccag tggctgctgc cagtggcgat aagtcgtgtc ttaccgggtt   9000
ggactcaaga cgatagttac cggataaggc gcagcggtcg ggctgaacgg ggggttcgtg   9060
cacacagccc agcttggagc gaacgaccta caccgaactg agatacctac agcgtgagct   9120
atgagaaagc gccacgcttc ccgaagggag aaaggcggac aggtatccgg taagcggcag   9180
ggtcggaaca ggagagcgca cgagggagct tccaggggga aacgcctggt atctttatag   9240
tcctgtcggg tttcgccacc tctgacttga gcgtcgattt ttgtgatgct cgtcaggggg   9300
gcggagccta tggaaaaacg ccagcaacgc ggccttttta cggttcctgg ccttttgctg   9360
gccttttgct cacatgttct ttcctgcgtt atcccctgat tctgtggata accgtattac   9420
cgccatgcat                                                          9430
```

<210> SEQ ID NO 7
<211> LENGTH: 26
<212> TYPE: DNA
<213> ORGANISM: Artificial Sequence

```
<220> FEATURE:
<223> OTHER INFORMATION: Upstream primer used for amplifying DHFR-TS

<400> SEQUENCE: 7

catccgcgga tgcagaaacc ggtgtg                                          26


<210> SEQ ID NO 8
<211> LENGTH: 26
<212> TYPE: DNA
<213> ORGANISM: Artificial Sequence
<220> FEATURE:
<223> OTHER INFORMATION: Downstream primer used for amplifying DHFR-TS

<400> SEQUENCE: 8

ctggatccaa gacagccatc tccatc                                          26


<210> SEQ ID NO 9
<211> LENGTH: 28
<212> TYPE: DNA
<213> ORGANISM: Artificial Sequence
<220> FEATURE:
<223> OTHER INFORMATION: Upstream primer used for amplifying histone 4
      upstream regulatory sequence

<400> SEQUENCE: 9

cagcatatga accagcaaag gtagcaac                                        28


<210> SEQ ID NO 10
<211> LENGTH: 27
<212> TYPE: DNA
<213> ORGANISM: Artificial Sequence
<220> FEATURE:
<223> OTHER INFORMATION: Downstream primer used for amplifying histone 4
      upstream regulatory sequence

<400> SEQUENCE: 10

ctaccgcggg ataccctgga tgttgtc                                         27


<210> SEQ ID NO 11
<211> LENGTH: 24
<212> TYPE: DNA
<213> ORGANISM: Artificial Sequence
<220> FEATURE:
<223> OTHER INFORMATION: Upstream primer used for amplifying yellow
      fluorescent protein gene and its downstream regulatory sequence

<400> SEQUENCE: 11

catccagggt atcggatcct gtcg                                            24


<210> SEQ ID NO 12
<211> LENGTH: 27
<212> TYPE: DNA
<213> ORGANISM: Artificial Sequence
<220> FEATURE:
<223> OTHER INFORMATION: Downstream primer used for amplifying yellow
      fluorescent protein gene and its downstream regulatory sequence

<400> SEQUENCE: 12

cgcaattgct tcacatggaa cccctgg                                         27


<210> SEQ ID NO 13
<211> LENGTH: 52
<212> TYPE: DNA
<213> ORGANISM: Artificial Sequence
<220> FEATURE:
<223> OTHER INFORMATION: Upstream primer used for amplifying TFP250

<400> SEQUENCE: 13
```

-continued

```
atcccgcggg cccgggatcc tgtcgccacc atggaattgc accccattcc ag           52


<210> SEQ ID NO 14
<211> LENGTH: 34
<212> TYPE: DNA
<213> ORGANISM: Artificial Sequence
<220> FEATURE:
<223> OTHER INFORMATION: Downstream primer used for amplifying TFP250

<400> SEQUENCE: 14

atttgcggcc gcctactgaa tgtcgccgct gtcg                               34
```

USE OF COCCIDIAN

TECHNICAL FIELD

The present invention relates to a novel use of coccidia, specifically relates to the use of the coccidia as a live vector of vaccine.

BACKGROUND ART

The recombinant vector vaccine developed by the use of transgenic technology with pathogenic micro-organisms as the vector, can prevent the attenuated vaccine strain getting strong again, but also generate cellular immune responses and has incomparable advantages over traditional vaccines. Currently, research at home and abroad is focusing on genetic recombinant vaccine with a live vector and its mechanism of action. An effective live vector vaccine I is required to have two conditions: first, being safe to host, second, being able to effectively express and deliver the protective antigen having immunocompetence.

At present, research-focused vaccine vectors comprise two categories: one category is attenuated viral vectors, such as the pox virus and adenovirus; the other is enteric pathogenic attenuated bacteria and symbiotic bacteria, such as *Salmonella* and lactic acid bacteria. Live virus vector can cause effective specific immune response through displaying exogenous antigen on the host cell surface or releasing it into the extracellular environment to make it be recognized by the host immune system. It is possible for the enteric pathogenic attenuated bacteria and symbiotic bacteria after the genetic modification to sustainably and efficiently express autoantigens and exogenous antigens in the host body, thus effectively stimulating protective mucosal immunity, humoral and cellular immune responses against pathogens and foreign antigens. There are inherent weaknesses for the attenuated viruses, enteric pathogenic bacteria and symbiotic bacteria as a live vaccine vector. As a vaccine vector, exogenous genetic fragment that viruses and bacteria can accommodate is small and difficult to carry out large-scale genetic modification. Viral vectors readily trigger host immune tolerance and are difficult to achieve the desired effect by oral administration. Enteric pathogens vectors such as *Salmonella* easily spread to other parts of the body in the host body, damage other organs and tissues, and cause immune tolerance due to persistent infection; some strains are zoonotic pathogens, which are released into the environment and pose a potential threat to the health of human and animals. In addition, bacterial vectors can not perform glycosylation for the expressed exogenous protein and other modifications, thus causing lack of immune activity of the expressed exogenous protein.

The use of eukaryotes as a carrier will undoubtedly have a greater advantage over viruses and prokaryotes. A larger eukaryotic vector genome can be carried out large-scale genetic modification. And in eukaryotic cells, proteins can be correctly folded and modified to express the target protein with normal activity. Although the challenge use of eukaryotic vectors faces is far greater than viruses and bacteria carriers, because it involves a more complex biological interactions, but since genomic and proteomic research has been relatively mature today, such research can be turned into reality from imagine.

It has been several decades since live oocyst vaccines prepared by blending a variety of attenuated chicken coccidian became available. At present its annual sales have been more than 300 million U.S. dollars, and in the prevention and treatment of coccidiosis in chickens it is playing an increasingly important role. Now study on the interaction between the host and the live oocysts of chicken coccidia vaccine, as well as the immune response mechanism against coccidiosis in the host has been in-depth. However, so far there is no report on application of chicken coccidia as live vector vaccine and application of other Eimeriidae generic coccidia and *Cryptosporidium* coccidia as live vector vaccine.

SUMMARY OF INVENTION

The object of the present invention is to provide a use of coccidiosis as live vaccine vector;

The other object of the present invention is to provide a live coccidia vector vaccine. Use of live coccidia vector vaccine according to the present invention to express the target protein can induce organism to simultaneously generate protective humoral and cellular immune responses (including the mucosal immune response) and generate memory responses.

The target gene is cloned into the expression vector having the drug selection marker or fluorescent selection marker, the recombinant vector is introduced into the cells of coccidia by electroporation or other transfection methods, then the integrated transgenic coccidia expressing target protein or stably transfected coccidia that contain expression vector and can express exogenous protein are obtained through drug screening, or flow cytometry screening. After inoculation of chicken or other poultry and mammals with transgenic coccidia or stably transfected coccidia as vaccine, when the coccidia express the target protein in the developing process, the protein expression in time and space are subjected to the regulation of the upstream and downstream sequences of the coccidia phased expression gene.

The coccidia vector in the present invention can be used to express spike glycoprotein such as *Eimeria maxima* TFP250 protein, avian influenza virus HA, and the like, and other external and internal antigen protein (HA, NA, NP, M1, M2, NS1, NS2, PA, PB1, and PB2 proteins), important antigen protein against pathogens such as Newcastle disease virus F protein and so on, thus causing the host's immune responses.

Expression vectors for transforming coccidia can be any expression vectors that can express exogenous protein in coccidian. The recombinant vectors in the present invention include pH4sp-HA1-EYFP-ACTIN, pH4SP-M2e-EYFP-ACTIN, $pH_{gra8}$-E-HA-A3', pHgra8-E-NA-A3', $pH_{gra8}$-E-NP-A3', pHDEA-TFP and so on. These vectors are used to transform coccidia, which are screened in order to obtain transgenic coccidia or stably transfected coccidian that can stably express the target protein. The obtained coccidia are orally administrated to immunized animals. As a result, it was found that the obtained coccidian have a significant immune effect on the coccidian and/or virus infection.

Live vaccine vector in the present invention is precocious attenuated or wild-type coccidia, preferably *Eimeria Wenyonella, Cryptosporidium* and so on. Chicken coccidia represented by *Eimeria tenella* are the preferred species, which can be used to carry out transgenic research and act as live vaccine vector.

Because coccidian haploid has about 14 chromosomes, its genome size reaches 60 Mb, therefore there are a considerable number of sites that can be used for integration, and the genome can allow insertion of large fragments of exogenous gene. Genetic flanking sequence of coccidia can be used to regulate the transcription of exogenous protective antigen gene, which will periodically express and secrete in the period of growth and development of the coccidia from the coccidia (using signal peptide of coccidia), thus obtaining transgenic coccidia that can stably express the target protein and stimulate a strong host humoral and cellular immune responses (including the mucosal immune response). Compared with bacterial and viral vaccine vectors, transgenic coccidia as a live vaccine vector has a unique advantage.

First, nuclear genome size of coccidia is about 60 Mb, which can accommodate large fragments of exogenous gene. Second, the coccidia are eukaryotes, which can express antigen protein modified by glycosylation. Third, the coccidia enter intestinal epithelial cells to form parasitophorous vacuole, causing the separation from host cell nucleus, so its genetic fragments holds little probability to insert or integrate into the host cell genome. Fourth, due to the protection of oocyst wall, after oral administration live oocyst vaccine of transgenic coccidia will effectively reach specific sites of intestinal or respiratory vaccines to play a role as vaccine and will not reduce the activity of the vaccine because of acid environment of the crop and the stomach and so on. Fifth, oral vaccination is simple and applicable to groups to carry out drinking water immunization or feed preparation immunization; since oocysts can be repeatedly infected under natural breeding conditions, one shot immunity is equivalent to several times of vaccination. Sixth, the coccidia have a short breeding cycle, and the infections are self-limiting, the coccidia are eliminated from the body after generation of oocysts, which does not cause immunotolerance problems. Seventh, various hosts of the coccidia have a strong specificity without cross-species transmission, and they are widely distributed in fields, release of transgenic coccidia in the field will not cause the spread of the kind of pathogen, hence have a high bio-security.

The establishment of live vaccine vector of the present invention marks the birth of a new type of vaccine. The invention, which expresses another one or more (type) antigens used in vaccine with live vaccine (live coccidia oocysts) as vector and simultaneously stimulate cellular immunity and humoral immunity (including mucosal immunity) against a variety of pathogens, is an a useful complement to the eukaryotic expression system; to express the target protein of organisms in coccidia adds a new research direction for Parasitology; the coccidia gene engineering vaccine based on the present invention can also be used in production, and can in a planned way control the incidence of coccidiosis in China, and make survival rate, weight gain and feed conversion of the immune animal be higher than or equal to production performance of animals that use anticoccidial drugs, thus allowing the broad masses of farmers to benefit, and the said vaccine is pollution-free without residue.

SPECIFIC MODE OF CARRYING OUT THE INVENTION

Figure 1:
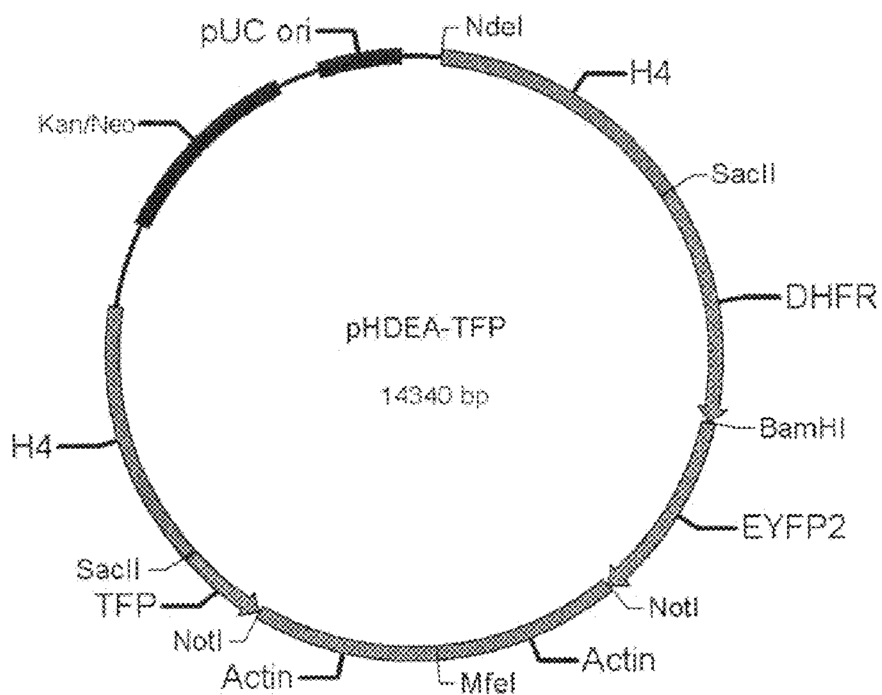
FIG. 1 is a constitutive schematic diagram of vector pHDEA-TFP, in which H4: *Eimeria tenella* histone 4 upstream regulatory sequence; DHFR: *Toxoplasma gondii* DHFR-TS gene coding region (for pyrimethamine resistance); EYFP2: Enhanced yellow-fluorescent protein gene coding region; Actin: *Eimeria* Actin gene downstream regulatory sequences. wherein, TFP is *Eimeria maxima* TFP250 genes, the insertion position of other antigen protein gene can be the same or different.
Figure 2:
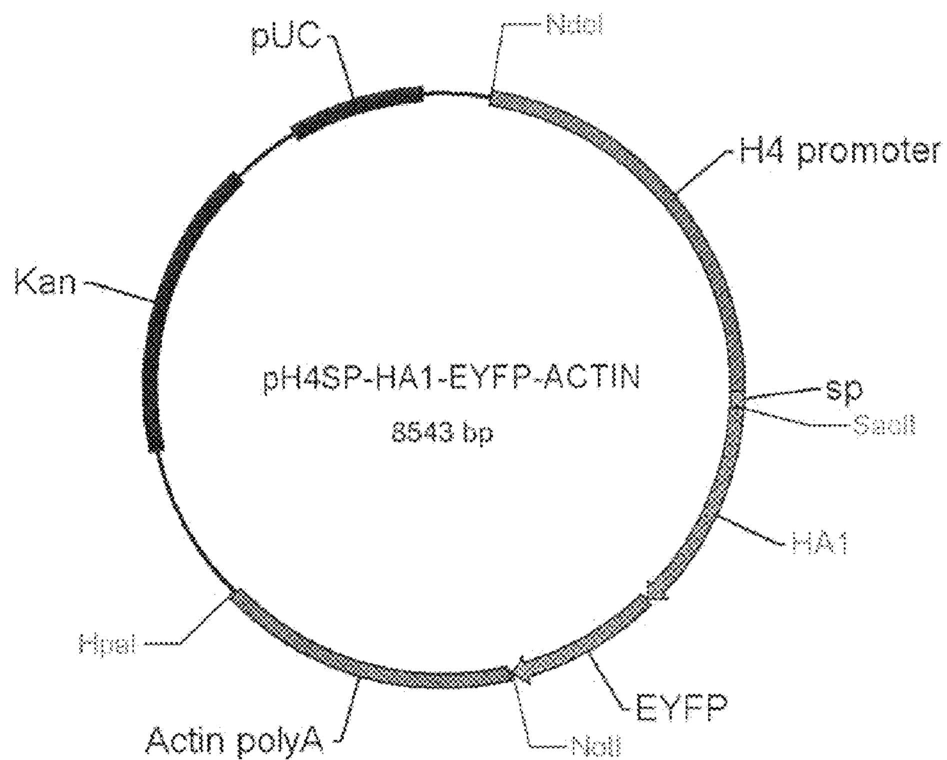
FIG. 2 is a constitutive schematic diagram of vector pH4sp-HA1-EYFP-ACTIN, in which, H4: *Eimeria tenella* histone 4 upstream regulatory sequence; SP: a signal peptide sequence of antigen 2 on the surface of *Eimeria tenella*, said sequence is 69 base pairs in length; HA1: H5N1 avian influenza virus HA antigen HA1 subunit; EYFP: enhanced yellow fluorescent protein gene coding region; Actin poly A: *Eimeria tenella* Actin gene downstream regulatory sequences.
Figure 3:
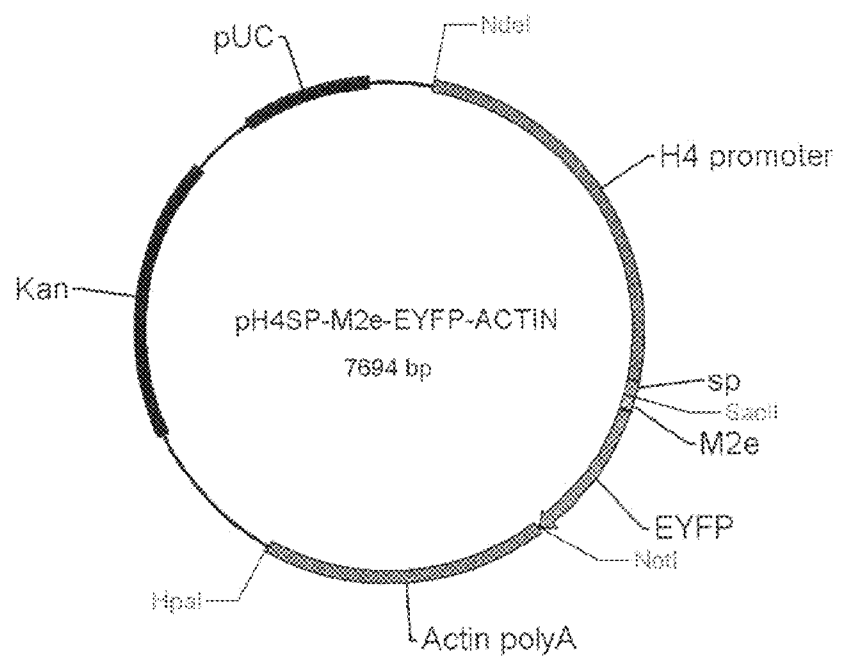
FIG. 3 is a constitutive schematic diagram of vector pH4SP-M2e-EYFP-ACTIN, in which, H4: *Eimeria tenella* histone 4 upstream regulatory sequence; SP: a signal peptide sequence of antigen 2 on the surface of *Eimeria tenella*, said sequence is 69 base pairs in length; M2e: extracellular domain of H5N1 avian influenza virus M2 antigen; EYFP: enhanced yellow fluorescent protein gene coding region; Actin poly A: *Eimeria tenella* Actin gene downstream regulatory sequences.
Figure 4:
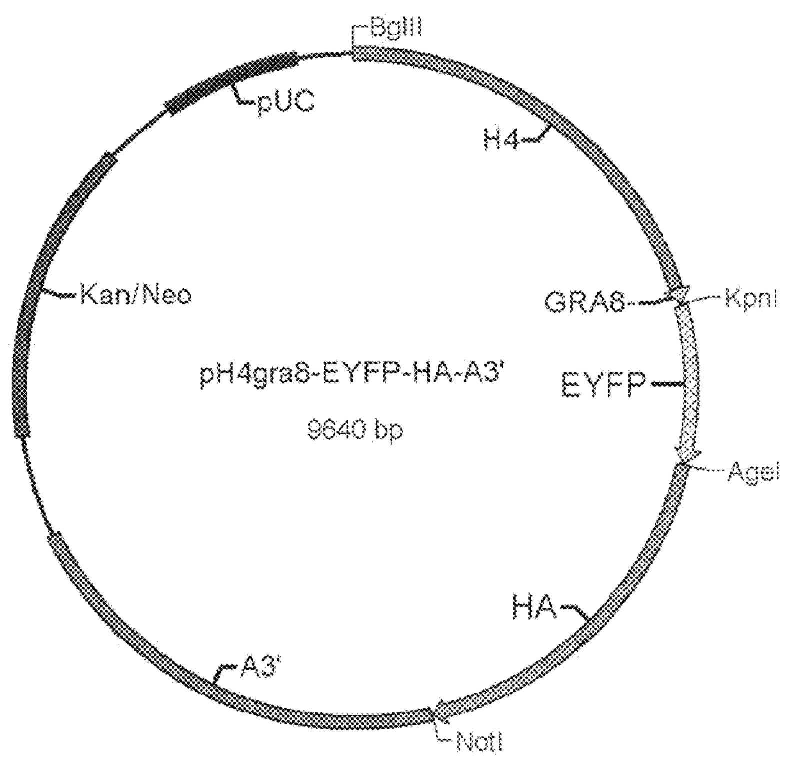
FIG. 4 is a constitutive schematic diagram of vector pHGRA8-E-HA-A3', in which, H4: *Eimeria tenella* histone 4 upstream regulatory sequence; GRA8*: Toxoplasma gondii* dense granule protein GRA8 signal peptide coding sequence; EYFP: yellow fluorescent protein gene coding region; HA: the gene encoding area of H5N1 avian influenza virus HA protein; A 3': *Eimeria tenella* Actin gene downstream regulatory sequences.
Figure 5:
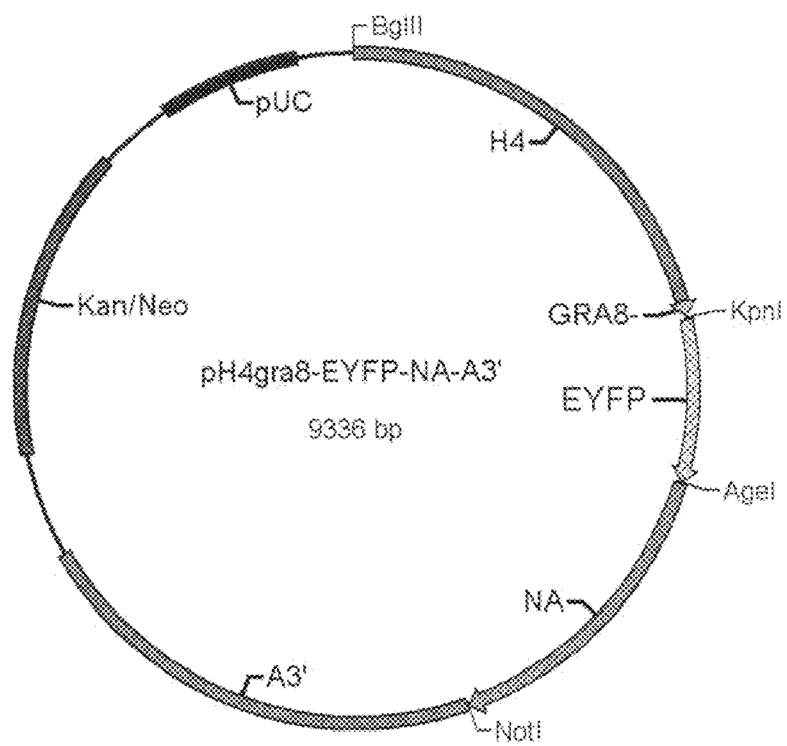
FIG. 5 is a constitutive schematic diagram of vector pHGRA8-E-NA-A3', in which, H4: *Eimeria tenella* histone 4 upstream regulatory sequence; GRA8*: Toxoplasma gondii* dense granule protein GRA8 signal peptide coding sequence; EYFP: yellow fluorescent protein gene coding region; NA: the gene encoding area of H5N1 avian influenza virus NA protein; A 3': *Eimeria tenella* Actin gene downstream regulatory sequences.
Figure 6:
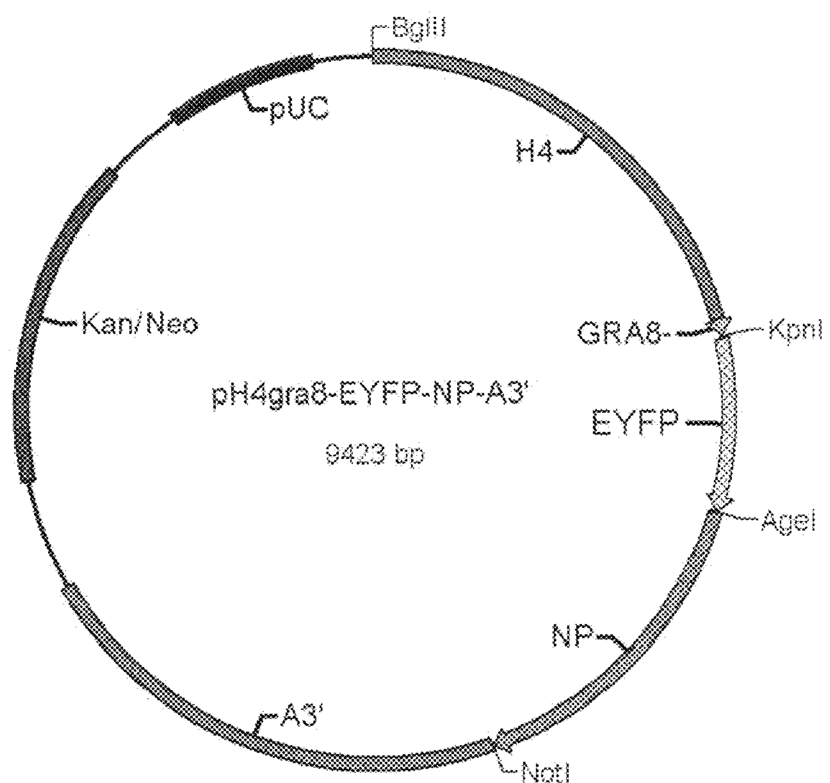
FIG. 6 is a constitutive schematic diagram of vector pHGRA8-E-NP-A3', in which, H4: *Eimeria tenella* histone 4 upstream regulatory sequence; GRA8*: Toxoplasma gondii* dense granule protein GRA8 signal peptide coding sequence; EYFP: yellow fluorescent protein gene coding region; NP: gene coding area of H5N1 avian influenza virus NP protein; A 3': *Eimeria tenella* Actin gene downstream regulatory sequences.

The present invention will be further illustrated in combination with specific examples. It should be understood that these examples are only intended to explain the present invention without limiting the scope of protection of the invention.

Example 1

The example is intended to use transgenic *Eimeria tenella* as a live vaccine vector to express the target gene, thus achieving simultaneous immunization of both the coccidia and certain pathogens.

*Eimeria maxima* TFP250 gene is taken as an example:

1. Constructing Expression Vector and Cloning the Target Gene into the Expression Vector 10-day-old chickens are inoculated with *Eimeria tenella* strain BJ125 (Suo Xun, Qu Hong-fei, LIU Zong-quan, Lin Kun-hua, Lu Yan-li. Late-maturing strains breeding and immunogenicity study of *Eimeria tenella.* 1996, 4 Journal of Agricultural Biotechnology (2), 78-79), after 6-9 days manure or intestinal contents of sick chicken are collected to obtain coccidia oocyst, after the sporogenesis the sporangia are extruded on slide glass, a sporangium is sucked up using capillary pipette under the microscope, namely, a single sporangium of *Eimeria* coccidia isolated therefrom, the proliferated oocysts are collected after oral infection of the chicken with the isolated single sporangia of coccidia, that is, purified genetic relatively consistent coccidia strains system is obtained. After purification of the obtained genetic relatively consistent *Eimeria tenella*, coccidia genome DNA is extracted with the general methods, coccidia gene regulatory sequence (histone 4 upstream regulatory sequence H4) is cloned using PCR method, *Eimeria maxima* TFP250 gene sequence is obtained using RT-PCR. The regulatory sequence H4, drug screening marker gene DHFR-TS, TFP250 and other components are constructed into the yellow fluorescence vector (purchased from BD Company), expression vector pHDEA-TFP required for *Eimeria tenella* transgene is constructed, the detailed contents are as follows:

Cloning *Toxoplasma gondii* DHFR-TS gene coding region: extracting total RNA of Toxoplasma gondii, amplifying and obtaining DHFR-TS gene using RT-PCR method, introducing restriction sites SacII and BamHI respectively at both ends, designing upstream and downstream primers (DHFR-UP: 5'-CATCCGCGGATGCAGAAACCGGTGTG-3' (SEQ ID NO.7); DHFR-L: 5'-CT GGATCCAAGACAGCCATCTCCATC-3' (SEQ ID NO.8)), obtaining DNA fragments with the size of 1.8 Kb, recovering target fragment and ligating it with the vector PGEM-T, transforming after overnight, extracting plasmids, identifying by enzyme digestion, introducing mutant site against pyrimethamine by PCR after DNA sequencing of the obtained candidate positive plasmids.

Cloning *Eimeria tenella* histone 4 upstream regulatory sequences and *Eimeria tenella* Actin gene downstream regulatory sequences: allowing the coccidia genomic DNA as a template, at both ends of the upstream regulatory sequence introducing restriction site NdeI and SacII (H4-UP: 5'-CAG CATATGAACCAGCAAAGGTAGCAAC-3' (SEQ ID.9); H4-L: 5'-CTACCGCGGGATACCCTGGATGTTGTC-3' (SEQ ID NO.10)) for amplification of H4 upstream regulatory sequence; at both ends of the yellow fluorescent protein gene and the downstream regulatory sequences introducing BamHI and MfeI sites, respectively designing primers (E2-UP: 5'-CATCCAGGGTATCGGATCCTGTC G-3' (SEQ ID NO.11); Actin-L: 5'-CGCAATTGCTTCACATGGAAC-CCCTGG-3' (SEQ ID NO.12)), which are amplified by PCR to obtain a yellow fluorescent protein gene and the downstream regulatory sequences. Respectively obtaining upstream regulatory sequence with the size of 2.0 kb and 2.9 kb and the DNA fragments of the downstream regulatory sequences fused with the yellow fluorescent protein, recovering target fragment and ligating it with the vector PGEM-T, transforming after overnight, extracting plasmids, identifying by enzyme digestion, carrying out DNA sequencing of the obtained candidate positive plasmids. cloning *Eimeria maxima* TFP250 gene: extracting the total RNA from *Eimeria maxima* and carrying out reverse transcription to obtain cDNA, during PCR amplication respectively introducing Not I and fused SacII and BamHI sites (T-UP: 5'ATC CCGCGGGCCCG GGATCCTGTCGCCACCATGGAATTGCACCCCATTCC AG 3' (SEQ ID NO.13); T-L: 5' ATTT GCGGCCGCCTACTGAATGTCGCCGCTGTCG 3' (SEQ ID NO.14)) at both ends of TFP250 and performing amplication, obtaining DNA fragments with the size of 660 bp, recovering target fragment and ligating it with the vector PGEM-T (purchased from Promega company), transforming after overnight, extracting plasmids, identifying by enzyme digestion, carrying out DNA sequencing for the obtained candidate positive plasmids.

Ligating each gene after digestion with yellow fluorescent vector after corresponding digestion, eventually obtaining the expression vector containing each component with its nucleotide sequence as shown in sequence list SEQ ID NO.1.

2. Transformation and Screening of Coccidia

The proliferated oocysts are collected after oral infection of the chicken with single oocysts of the preservative *Eimeria tenella,* 15 days old chickens are inoculated with the above-mentioned oocysts, 200-500 oocysts for each chicken. The discharged coccidia oocysts are collected and purified after 6 to 9 days, in this way continuous passages are done, the obtained oocysts are the oocysts required for constructing a vector.

By electroporation the constructed pHDEA-TFP is transfected into the sporozoites of *Eimeria tenella*, which is inoculated in ileocecal opening of the chicken through cloaca, while specific pyrimethamine resistance screening drugs are added. Specifically, $1\times10^7$ precocious strain sporozoites are taken, 50 μg of pHDEA-TFP plasmids are added, in which shock condition is 2 kv, capacitance is 25, shock time is 0.3 ms, after standing for 20 min, the transfected sporozoite are inoculated again in ileocecal opening of the chicken through cloaca. After 24 hours of incubation the selected pressure is exerted, namely, the specific pyrimethamine resistance screening drugs are added, the test is observed under fluorescence microscope.

Transgenic coccidia line or stably transfected coccidia line capable of stable expression can be obtained by repeating this process. Under fluorescence microscope it will be observed that transgenic coccidia capable of stable expression or the polypide of stably transfected coccidia line can emit yellow fluorescence, luminescence rate is higher than 99%.

3. Inoculation of Chickens

First, the oocysts are sporulated in vitro, the 1-5 day-old healthy chickens are choosed to be orally inoculated with the breeding early-maturing strains or wild-type transgenic coccidia or sporulated oocysts of stably transfected coccidia Coccidia sporulated coccidia, 200-500/chicken, after 5-7 days the chickens are detected for clinical manifestations, the number of oocysts per gram (OPG), pathological grading and other indices.

4. The Effect

After inoculation it is founded that the transgenic coccidia or stably transfected coccidia have good immunogenicity against *Eimeria tenella* and *Eimeria maxima*, or other pathogenic infections, Seven-day-old AA broiler chickens are inoculated with the oocysts of transgenic coccidia, $1.0\times10^3$ oocyst/chicken, at the fourteenth day after inoculation, after attacking-coccidia, the number of oocysts discharged from per chicken was significantly lower than those in non-immunized groups without attacking-coccidia ($P<0.05$), and there is no significant difference between the attacking-coccidia group and the group immunized with parent strain oocysts with the same dose ($P>0.05$). It indicates that inoculation with the transgenic coccidian, $1.0\times10^3$ oocyst/chicken, can provide seven-day-old chicks with immunoprotection. Another immune procedure is to use low-dose immunization of transgenic coccidia oocysts, 200 oocysts/chicken, to immunize 4-day-old AA broiler chickens, at the fourteenth day after immunizing two times, the AA broiler chickens are attacked with transgenic coccidia and parent strain oocysts, $1.0\times10^3$ oocyst/chicken, only to find the minimal amount of fecal oocysts are discharged along with Faeces, the oocyst production per chicken is significantly lower than those in non-immunized groups without attacking-coccidia ($P<0.01$), similar with the groups immunized with parent strains, the chickens in the group immunized with the transgenic coccidian two times are completely protected. The data from two kinds of immune schemes indicate that the expression of exogenous genes does not affect the immunogenicity of the transgenic coccidia. After inoculation, the pathological grading, oocyst production of coccidia in the infected chickens and cecal lesion values all decrease, the decline of weight gain of chickens is improved, OPG value is $6\times10^4$-$6\times10^6$, a good immune protection is generated to prevent lethal dose of coccidia attack or the challenged infections induced by other pathogens.

Example 2 pH4sp-HA1-EYFP-ACTIN, pH4SP-M2e-EYFP-ACTIN, $pH_{gra8}$-E-HA-A3', $pH_{gra8}$-E-NA-A3' and $pH_{gra8}$-E-NP-A3' expression vector are constructed respectively according to the method similar to the above-mentioned methods, which are then transformed into the coccidia, followed by obtaining the coccidia that can stably express the target gene through screening. Cohabitation infection test indicates that the obtained coccidia have high protective rate against coccidian infection and virus infection (>90%).

INDUSTRIAL APPLICABILITY

The present invention provides a novel use of coccidia, specifically relates to the use of coccidia as a live vaccine vector. The present invention further provides a live vaccine with coccidia as a vector, which is transgenic coccidia capable of expressing exogenous protein or stably transfected coccidia that contain expression vector and can express exogenous coccidia. The present coccidia vector live vaccine can induce organisms to simultaneously generate protective humoral and cellular immune responses (including the mucosal immune response) and generate memory responses, which can be readily carried out and has stable effect and high biological safety without generating immune tolerance. The coccidia gene engineering vaccine based on the present invention can also be used in production, and can in a planned way control the incidence of coccidiosis in China, and make survival rate, weight gain and feed conversion of the immune animal be higher than or equal to production performance of animals that use anticoccidial drugs, thus allowing the broad masses of farmers to benefit, and the said vaccine is pollution-free without residue.

The description of the sequences:

SEQ ID NO.1~6 are in sequence: full sequences of expression vector pHDEA-TFP, pH4sp-HA1-EYFP-ACTIN, pH4SP-M2e-EYFP-ACTIN, pHgra8-EYFP-HA-A3', pHgra8-EYFP-NA-A3' and pHgra8-EYFP-NP-A3'.

What is claimed is:

1. A coccidian vector live vaccine, formed of a stably transfected coccidia that contains an expression vector and can express a target protein, said target protein being an antigen protein of pathogens, and said expression vector being pHDEA-TFP as shown in SEQ ID NO. 1.

2. A coccidian vector live vaccine formed of a stably transfected coccidia that contains an expression vector and can express a target protein, said target protein being an antigen protein of pathogens, and said expression vector being selected from pH4sp-HA1-EYFP-ACTIN as shown in SEQ ID NO. 2, pH4SP-M2e-EYFP-ACTIN as shown in SEQ ID NO. 3, Phgra8-E-HA-A3', gra8pH-E-NA-A3' as shown in SEQ ID NO. 4, or pHgra8-E-NP-A3' as shown in SEQ ID NO. 5.

3. The coccidian vector live vaccine as claimed in claim 1, wherein the said coccidia are Eimeriidae coccidian or *Cryptosporidium* coccidian.

4. The coccidian vector live vaccine of claim 2, wherein the said coccidia are Eimeriidae coccidian or *Cryptosporidium* coccidian.

5. A method of inducing an immune response in an organism, the method comprising:

administering a vaccine live vector to an organism, wherein said vaccine live vector is the coccidian vector live vaccine as claimed in claim 1.

6. The method as claimed in claim 5, wherein the said coccidia are Eimeriidae coccidian or *Cryptosporidium* coccidian.

7. The method as claimed in claim 6, wherein said coccidia are Eimeriidae coccidian or *Cryptosporidium* coccidian of poultry or mammals.

8. The method as claimed in claim 1, wherein said stably transfected coccidia can timely and spatially control the expression of the target protein.

9. A method of inducing an immune response in an organism, the method comprising:

administering a vaccine live vector to an organism, wherein said vaccine live vector is the coccidian vector live vaccine as claimed in claim 2.

* * * * *